US006682740B1

(12) United States Patent
Erdei et al.

(10) Patent No.: US 6,682,740 B1
(45) Date of Patent: Jan. 27, 2004

(54) PEPTIDES DERIVED FRAM COMPLEMENT PEPTIDE C3A SEQUENCE AND ANTIALLERGIC COMPOSITIONS COMPRISING THEM

(75) Inventors: Anna Erdei, Budapest (HU); Israel Pecht, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 233 days.

(21) Appl. No.: 09/708,606

(22) Filed: Nov. 9, 2000

Related U.S. Application Data

(63) Continuation-in-part of application No. 09/446,464, filed as application No. PCT/IL98/00292 on Jun. 22, 1998, now abandoned.

(30) Foreign Application Priority Data

Jun. 22, 1997 (IL) ................................................ 121134

(51) Int. Cl.[7] ................................................ A61K 45/00

(52) U.S. Cl. ................................ 424/185.1; 424/278.1; 514/12; 514/13; 514/14; 514/15; 514/16; 514/17; 530/324; 530/325; 530/326; 530/327; 530/328; 530/329; 530/330

(58) Field of Search ............. 514/12–17; 530/324–330; 424/278.1, 185.1

(56) References Cited

PUBLICATIONS

Dufosse, J. et al. (1993) Biochem. J. 293:329–337.*

Abaza et al. J. (1992) Protein Chemistry, 11(5):433–444.*

Erdei et al., "Complement peptide C3a inhibits of IgE–mediated triggering of rat mucosal mast cells" International Immunology, vol. 7, No. 9, pp. 1433–1439, (1995).

Erdei et al., "Complement peptides and mast cell triggering", Immunology Letters vol. 54, pp. 109–112, (1996).

Erdei et al., "Role of C3a and C5a in the Activation of Mast Cells", *Exp. Clin. Immunogenet.*, vol. 14 pp. 16–18, (1997).

Erdei et al., "Inhibition of IgE–mediated triggering of mast cells by complement–derived peptides interacting with the Fc3RI"*Immunology Letters*, vol. 68, pp. 79–82, (1999).

Morgan et al., "Suppression of Humoral Immune Responses by Synthetic C3a Peptides", *J. Immunol*, vol. 131 pp. 2258–2261, (1983).

Gerardy et al., "Design and biological activity of a new generation of synthetic C3a analogues by combination of peptidic and non–peptidic elements", *Biochem. J.*, vol. 255, pp. 209–216, (1988).

Ember et al., "Designing synthetic superantagonists of C3a anaphylatoxin", *Biochemistry*, vol. 30, pp. 3603–3612, (1991).

Mousli et al., "Peptidergic pathway in human skin and rat peritoneal mast cell activation", *Immuno.*, vol. 27 pp. 1–11, (1994).

Oppermann et al., "C3a activates reactive oxygen radical species production and intracellular calcium transients in human eosinophils", *Eur. J. Immunol.*, vol. 24, pp. 518–522, (1994).

Mousli et al., "A mechanism of action for anaphylatoxin C3a stimulation of mast cells", *J. Immunol.*, vol. 148 pp. 2456–2461, (1992).

* cited by examiner

*Primary Examiner*—Christina Chan
*Assistant Examiner*—F. Pierre Vander Vegt
(74) *Attorney, Agent, or Firm*—Browdy and Neimark, P.L.L.C.

(57) ABSTRACT

Peptides corresponding partially or entirely to positions 50–77 of the sequence of the complement-derived peptide C3*a* and analogs thereof are capable of inhibiting IgE-mediated triggering and/or the FcεRI-induced secretory response of mucosal mast cells. These peptides are useful for prevention and/or treatment of allergic disorders caused by IgE mediated (Type I) hypersensitivity where mucosal-type mast cells are involved, such as hay fever, asthma, some cases of urticaria or allergic conjunctivitis.

17 Claims, 11 Drawing Sheets

PEPTIDES DERIVED FRAM COMPLEMENT PEPTIDE C3A SEQUENCE AND ANTIALLERGIC COMPOSITIONS COMPRISING THEM

CROSS-REFERENCE TO RELATED APPLICATIONS

The present application is a continuation-in-part of U.S. application No. 09/446,464, filed Dec. 22, 1999, now abandoned, which is a §371 national phase application of PCT/IL98/00292, filed Jun. 22, 1998, both of which are hereby incorporated by reference in their entirety.

FIELD OF THE INVENTION

The present invention is in the field of allergy and relates to peptides derived from the complement peptide C3a and to their use in the prevention and treatment of allergies.

BACKGROUND OF THE INVENTION

Mast cells and basophils play a central role in inflammatory and immediate hypersensitivity reactions.

Clustering of the type 1 Fcϵ receptors (FcϵRI) present in their plasma membranes initiates a coupling cascade culminating in the secretion of mediators of immediate-type allergic reactions (Schwartz, 1994). The molecular mechanism of signal transduction initiated by FcϵRI clustering has been studied intensely over the past few years (Ravetch et al, 1991; Holowka et al, 1992; Benhamou et al, 1992; Beaven et al, 1993). The β and γ subunits of the clustered FcϵRI were found to interact with src family protein tyrosine kinases (PTK) and cause the so far earliest detected biochemical event in their cascade, i.e., their activation. The differential control of these PTK by the β and γ chains of the receptor has also been described recently (Jouvin et al, 1994). The following steps downstream involve recruitment of PTK of the syk family, activation of phospholipase Cγ, which in turn leads to hydrolysis of phosphatidyl inositides and production of inositol triphosphate and diacylglycerol. The former product causes the transient increase in free cytosolic calcium ion concentration while the latter is involved in activation of protein kinase C (Ravetch et al, 1991; Holowka et al, 1992; Benhamou et al, 1992; Beaven et al, 1993).

Two types of mast cells differentiate from a common precursor to produce the so-called serosal (or connective tissue type) and the mucosal type mast cells. Both phenotypes express FcϵRI on their cell membrane; however, they respond differently to secretagogues and inhibitors. For example, only serosal-type mast cells are triggered by cationic peptides (including the complement-derived peptides C3a and C5a; venom-peptides, e.g., mastoparan, mellitin; neuropeptides) or polyamines; mucosal mast cells are non-responsive to these stimuli (Mousli et al, 1994). In comparison to the advanced understanding of the coupling cascade initiated by FcϵRI clustering, the action modes of the complement-derived peptides C3a and C5a are less well understood.

As mentioned above, clustering of the FcϵRI on mast cells and basophils is known to trigger the secretory response of these effector cells central to the allergic reactions. Similarly, the anaphylatoxic activity of the complement-derived peptides C3a and C5a is also well-known, causing activation of serosal type mast cells that results in the release of histamine or serotonin and several other inflammatory mediators including proteases, lipid mediators and several cytokines (Schwartz, 1994).

Cellular events triggered in mast cells and basophils upon FcϵRI clustering or by complement-derived peptides have been investigated so far only as independent physiological processes. However, in vivo, both stimuli might be exerted simultaneously.

In earlier experiments carried out by the inventors of the present application, both the secretory response and biochemical coupling processes initiated by FcϵRI clustering of rat mucosal mast cells of the line RBL-2H3, which is non-responsive to complement-derived peptides, were investigated in the presence of a range of human C3a concentrations. It was found that C3a inhibits dose-dependently antigen-induced degranulation of the mucosal line RBL-2H3 while C5a applied in the same amounts had no effect at all. When added alone, none of the complement-peptides C3a and C5a triggered the secretory response of the rat mucosal-type cells of the line RBL-2H3 (Erdei et al, 1995).

Several steps coupling the FcϵRI-mediated stimulus to the secretory response were tested in order to try and identify at which point of the cascade C3a interferes. It was found that neither antigen binding to IgE-sensitized cells nor the reaction of FcϵRI with IgE were influenced by the complement peptide C3a. However, the tested intracellular events were strongly and dose-dependently inhibited by C3a, i.e., tyrosine phosphorylation of several cellular proteins, the activity of PLCγ, resulting in the inhibition of antigen-induced hydrolysis of phosphatidyl inositides, and elevation of intracellular free $Ca^{2+}$. RBL-2H3 cells proved to be unresponsive to C3a in all these tests.

The fragment C3a, also called anaphylatoxin, is not suitable for use as an anti-allergic drug because it is anaphylatoxic to serosal mast cells, i.e., it is capable of causing mediator release from this type of mast cells.

SUMMARY OF THE INVENTION

It has now been found in accordance with the present invention that certain peptides comprised partially or entirely within the sequence of positions 50–77 of the complement-derived peptide C3a, and analogs thereof, are capable of inhibiting the FcϵRI-induced secretory response of mucosal mast cells, without having the anaphylatoxic effect of C3a to mucosal mast cells.

Peptide C3a is a 77-mer peptide of the sequence:

Ser-Val-Gln-Leu-Thr-Glu-Lys-Arg-Met-Asp-Lys-Val-Gly-Lys-Tyr-Pro-Lys-Glu-Leu-Arg-Lys-Cys-Cys-Glu-Asp-Gly-Met-Arg-Glu-Asn-Pro-Met-Arg-Phe-Ser-Cys-Gln-Arg-Arg-Thr-Arg-Phe-Ile-Ser-Leu-Gly-Glu-Ala-Cys-Lys-Lys-Val-Phe-Leu-Asp-Cys-Cys-Asn-Tyr-Ile-Thr-Glu-Leu-Arg-Arg-Gln-His-Ala-Arg-Ala-Ser-His-Leu-Gly-Leu-Ala-Arg (SEQ ID NO:1)

The present invention relates to a peptide corresponding partially or entirely to the 50–77 sequence of the complement-derived peptide C3a and to analogs thereof capable of inhibiting IgE-mediated triggering and/or the FcϵRI-induced secretory response of mucosal mast cells, said peptides being selected from the sequences:

(a) X1-Cys-Asn-R1-Ile-Thr-R2-Leu-R3-R4-Gln-His-R5-R6-R7-R8-R9-R10-Gly-Leu-Ala-R11 (SEQ ID NOs:2–4);

(b) X1-Cys-Asn-R1-X4 (SEQ ID NOs:5–13);

(c) X2-Lys-Val-Phe-Leu-Asp-X3 (SEQ ID NOs:14–17; and (d) X5-Asp-Ser-Ser-Asn-Tyr-Ile-R11 (SEQ ID NO:18) wherein X1 is H, lower alkanoyl, Cys, Asp-Cys or Arg-Arg-Cys;

X2 is H, lower alkanoyl or Lys;

X3 is Arg or a sequence selected from (i) Ala-Ala-Asn-R1-Ile-Thr-R2-Leu-R3-R4 (residues 7–16 of SEQ ID NO:15);

(ii) Cys-Cys-Asn-R1-Ile-Thr-R2-Leu-R3 (residues 7–15 of SEQ ID NO:16); and (iii) Cys-Cys-Asn-R1-Ile-Thr-R2-Leu-R3-R4-Gln-His-R5-R6 (residues 7–20 of SEQ ID NO:17);

X4 is Gly, (i) Ile-Thr-R2-Leu-R3 (residues 5–9 of ID NO:6); or (ii) Ile-Thr-Arg-R11 (residues 5–8 of SEQ ID 7);

X5 is H, lower alkanoyl or Leu;

R1 is an aromatic amino acid residue;

R2 is Glu or Lys;

R3 is a positively charged amino acid residue;

R4 is Arg or Glu;

R5 is Ala or Arg;

R6 is Arg or Lys;

R7 is Ala or Asp;

R8 is Ser or His;

R9 is His or Val;

R10 is Leu, Ile, Ala or Gly; and

R11 is OH, Arg, Arg-$NH_2$, or Agm (agmatine);

and chemical derivatives and pharmaceutically acceptable salts thereof.

The peptide of the invention has preferably at least 5, more preferably 5, 7–8 or 20–21, and at most 28, amino acid residues. According to the invention, R1 is an aromatic amino acid residue preferably selected from Phe, Tyr, His and Trp; and R3 is a positively charged amino acid residue preferably selected from Arg, D-Arg, Har (homoarginine) and Lys. Lower alkanoyl according to the invention has preferably 1–4 carbon atoms, e.g., formyl, acetyl, propanoyl and butyryl.

In one embodiment, the peptide of the invention is the peptide herein identified as peptide C3a2, a 21-mer corresponding to the 57–77 sequence of the human complement peptide C3a, or the amide thereof, of the sequence:

Cys-Asn-Tyr-Ile-Thr-Glu-Leu-Arg-Arg-Gln-His-Ala-Arg-Ala-Ser-His-Leu-Gly-Leu-Ala-Arg (residues 57–77 of SEQ ID NO:1)

In another embodiment, the peptide of the invention is the peptide herein identified as peptide rC3a2, a 21-mer corresponding to the 57–77 sequence of the rat complement peptide C3a, or the amide thereof, of the sequence: Cys-Asn-Tyr-Ile-Thr-Lys-Leu-Arg-Glu-Gln-His-Arg-Arg-Asp-His-Val-Leu-Gly-Leu-Ala-Arg (SEQ ID NO:19)

In a further embodiment, the peptide of the invention is the peptide herein identified as peptide C3a2-R, a 20-mer corresponding to the 57–76 sequence of the human complement peptide C3a, or the amide thereof, of the sequence:

Cys-Asn-Tyr-Ile-Thr-Glu-Leu-Arg-Arg-Gln-His-Ala-Arg-Ala-Ser-His-Leu-Gly-Leu-Ala (residues 57–76 of SEQ ID NO:1)

In yet a further embodiment, the peptide of the invention is the peptide herein identified as peptide C3a9, a 8-mer analog corresponding to the 55–62 sequence of the human complement peptide C3a (with Glu62 changed to Arg), or the amide thereof, of the sequence:

Asp-Cys-Cys-Asn-Tyr-Ile-Thr-Arg (SEQ ID NO:20)

In still a further embodiment, the peptide of the invention is the peptide herein identified as peptide C3all, a 7-mer analog corresponding to the 55–61 sequence of the human complement peptide C3a (with Cys56 and Cys57 each changed to Ser and Thr61 changed to Arg), or the amide thereof, of the sequence:

Asp-Ser-Ser-Asn-Tyr-Ile-Arg (SEQ ID NO:21)

In yet another embodiment, the peptide of the invention is the peptide herein identified as peptide C3a13, a 5-mer analog corresponding to the 56–60 sequence of the human complement peptide C3a (with Ile60 changed to Gly), or the amide thereof, of the sequence:

Cys-Cys-Asn-Tyr-Gly (SEQ ID NO:22)

In still further embodiments, the peptides of the invention are the 14-mer C3a4, 20-mer C3a5, 15-mer C3a6, 9-mer C3a7, 7-mer C3a8, 10-mer C3a10, and 6-mer C3a12 and the 7-mer C3a14-P peptides, or the amides thereof, of the sequences:

C3a4: Lys-Val-Phe-Leu-Asp-Cys-Cys-Asn-Tyr-Ile-Thr-Glu-Leu-Arg (residues 51–64 of SEQ ID NO:1)

C3a5: Lys-Lys-Val-Phe-Leu-Asp-Cys-Cys-Asn-Tyr-Ile-Thr-Glu-Leu-Arg-Arg-Gln-His-Ala-Arg (residues 50–69 of SEQ ID NO:1)

C3a6: Lys-Val-Phe-Leu-Asp-Ala-Ala-Asn-Tyr-Ile-Thr-Glu-Leu-Arg-Arg (SEQ ID NO:23)

C3a7: Cys-Cys-Asn-Tyr-Ile-Thr-Glu-Leu-Arg

C3a8: Lys-Val-Phe-Leu-Asp-Arg (residues 56–64 of SEQ ID NO:1)

C3a10: Arg-Arg-Cys-Cys-Asn-Tyr-Ile-Thr-Arg-Arg (SEQ ID NO:25)

C3a12: Asp-Cys-Cys-Asn-Tyr-Gly (SEQ ID NO:26)

C3a14-P: Asp-Ser-Ser-Asn-Tyr-Ile-Thr-Arg (SEQ ID NO:27)

The invention further relates to pharmaceutical compositions comprising at least one peptide of the invention, a chemical derivative or a pharmaceutically acceptable salt thereof, and a pharmaceutically acceptable carrier, for the prevention and/or treatment of allergic disorders caused by IgE mediated (Type I) hypersensitivity where mucosal-type mast cells are involved such as hay fever, asthma rhinitis, some cases of urticaria, allergic conjunctivitis, and the like.

The invention further relates to a method for the prevention and/or treatment of allergic disorders caused by IgE mediated (Type I) hypersensitivity where mucosal-type mast cells are involved, which method comprises administering to an individual in need thereof an effective amount of a peptide of the invention, a chemical derivative or a pharmaceutically acceptable salt thereof.

BRIEF DESCRIPTION OF THE DRAWING

FIG. 4A shows results using 1.5 ng/ml of antigen, and FIG. 4B shows results using 0.7 ng/ml of antigen.

DETAILED DESCRIPTION OF THE INVENTION

Figure 1:
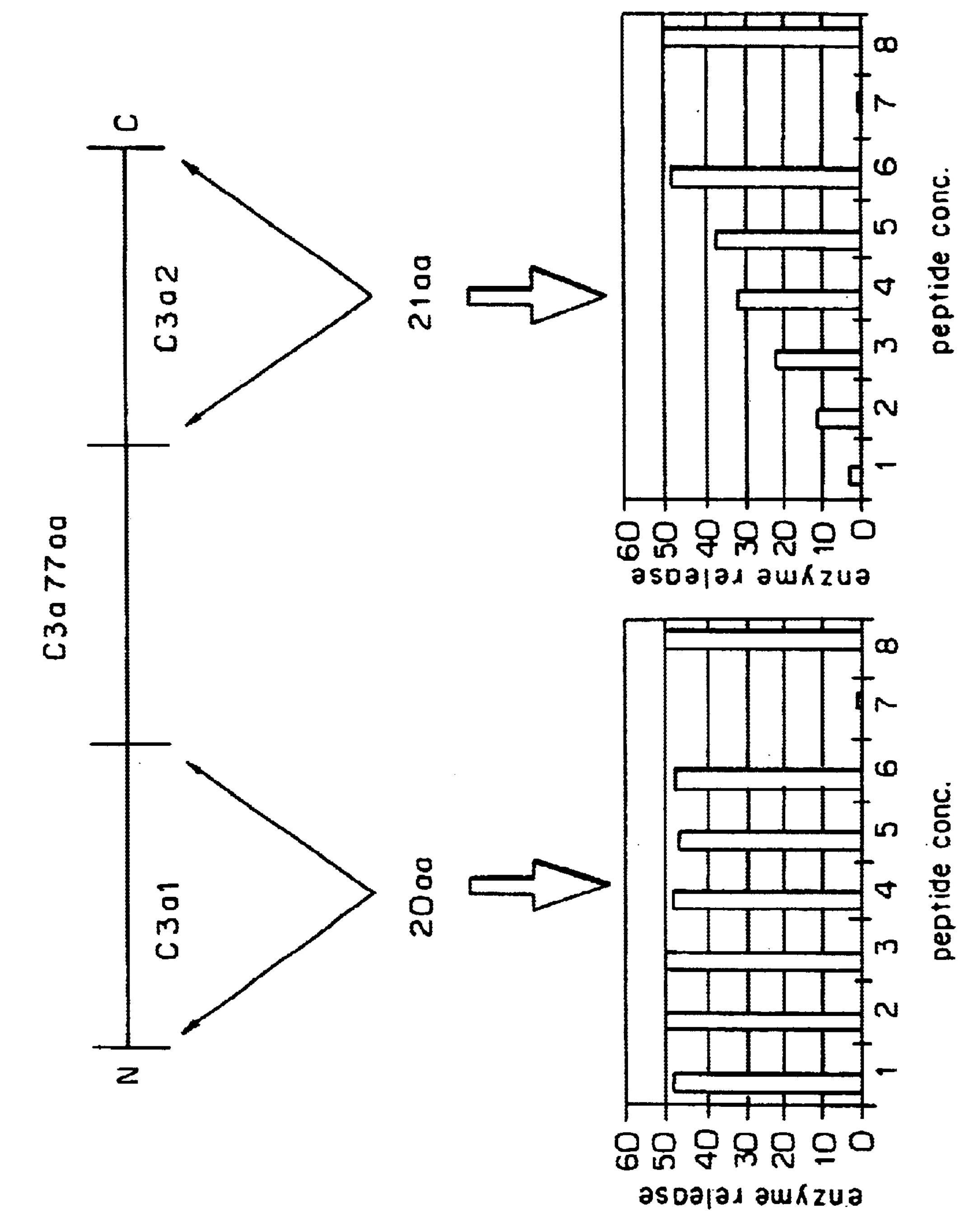
FIG. 1 depicts inhibition of antigen-induced degranulation of rat mucosal mast cells RBL-2H3 by the peptides comprising the C-terminal (peptide C3a2, positions 57–77) and N-terminal (peptide C3a1, positions 1–20) sequences of human complement peptide C3a, as described in Example 2 herein. In the figure, "aa" stands for "amino acids" and the "enzyme release" is presented as net percentages of the cells' total β-hexosaminidase activity.

The present invention relates to synthetic peptides based on the C-terminal sequence of the human complement C3a fragment, analogs and chemical derivatives thereof, and pharmaceutically acceptable salts of the foregoing.

The peptides of the invention are derived partially or entirely from the 50–77 sequence of the human complement C3a fragment as follows:

Lys-Lys-Val-Phe-Leu-Asp-Cys-Cys-Asn-Tyr-Ile-Thr-Glu-Leu-Arg-Arg-Gln-His-Ala-Arg-Ala-Ser-His-Leu-Gly-Leu-Ala-Arg (residues 50–77 of SEQ ID NO:1)

and to analogs thereof, in which the 50–55 or 50–56 sequence may be absent and the resulting Cys residue at the N-terminal position 56 or 57 may be acylated by a non-polar lower carboxylic acyl group such as formyl, acetyl, propanoyl and butyryl; the Cys-Cys residues at positions 56–57 may be replaced by Ala-Ala or Ser-Ser; the Tyr residue at position 59 may be substituted by another aromatic amino acid residue such as Phe, Trp and His; the Ile residue at position 60 may be replaced by Gly; the Thr at position 61 may be replaced by Arg; the Glu residue at position 62 may be replaced by Lys or Arg; the Leu residue at position 63 may be replaced by Arg; the Arg residue at position 64 may be substituted by D-Arg, a homoarginine residue (Har) or by Lys; the Arg residue at position 65 may be replaced by Glu; the Ala residue at position 68 may be replaced by Arg; the Arg residue at position 69 may be replaced by Lys; the Ala residue at position 70 may be replaced by Asp; the Ser residue at position 71 may be replaced by His; the His residue at position 72 may be replaced by Val; the Leu residue at position 73 may be replaced by Ile, Ala or sy; the Arg residue at position 77 may be absent or may be replaced by agmatine; and the Lys residue at position 50 and/or the sequences 50–53, 50–54, 50–55, 50–56, 61–77, 62–77, 63–77, 64–77, 65–77, 66–77, 70–77, and/or 57–77 may be absent. Arg or Arg-Arg can be added at the N-terminus or C-terminus of any of the above peptides or analogs, particularly where an Arg residue is not already present at the N- or C-terminus.

The C-terminus of the peptides of the invention may be presented in the free carboxy form or, preferably, it is amidated to facilitate the synthesis and increase the resistance of the peptides to enzymatic cleavage in the organism.

Other analogs and derivatives of the peptides may be selected for use in the invention by use of the well-known tests described hereinafter in Materials and Methods, sections (d)–(i), such as inhibition of antigen-induced secretory response of rat mucosal RBL-2H3 cells described in section (d), whereby an analogous peptide or a chemical derivative thereof that inhibits the antigen-induced release of the granular enzyme β-hexosaminidase by the RBL-2H3 cells may be suitable for use as anti-allergic according to the invention.

Also included within the scope of the invention are salts of the peptides and analogs of the invention. As used herein the term "salts" refers to both salts of carboxyl groups and to acid addition salts of amino groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as sulfuric or hydrochloric acid, or organic acids such as, for example, oxalic acid.

A "chemical derivative" as used herein refers to peptides containing additional chemical moieties not normally a part of the peptide molecule such as esters and amides of free carboxy groups, acyl and alkyl derivatives of free amino groups, esters and ethers of free hydroxy groups. Such modifications may be introduced into the molecule by reacting targeted amino acid residues of the peptide with an organic derivatizing agent that is capable of reacting with selected side chains or terminal residues. The added chemical moieties are not such as to change one amino acid residue to a different amino acid residue.

Both the salts and the chemical derivatives of the peptides are preferably used to modify the pharmaceutical properties of the peptides insofar as stability, solubility, etc., are concerned.

The invention further includes pharmaceutical compositions comprising a peptide of the invention, a chemical derivative thereof or a pharmaceutically acceptable salt thereof, together with a pharmaceutically acceptable carrier.

The peptides of the invention are intended for the prevention and/or treatment of allergic disorders caused by IgE-mediated (Type I) hypersensitivity where mucosal-type mast cells are involved, such as hay fever, asthma, some cases of urticaria and allergic conjunctivitis. Any suitable route of administration is encompassed by the invention such as oral, intravenous, intramuscular, subcutaneous, inhalation, intranasal, intradermal or other known routes. For the treatment of hay fever, for example, pharmaceutical compositions in the form of spray may be appropriate for administration in the pollen-season to prevent the development of allergy, as shown in recent clinical studies (Bentley et al, 1992; Juliusson et al, 1995) that mucosal-type mast cells infiltrate the nasal epithelium in patients with hay fever in the pollen season. Moreover, it is well known that the bronchial mucosal surface is the first contact site for inhaled allergens and, consequently, the response of the mucosal-type mast cells to the inhibitory peptides of the invention administered as spray may be very effective.

The invention will now be illustrated by the following non-limiting examples.

EXAMPLES

Material and Methods

Peptide Synthesis. The peptides were synthesized by the solid phase technique utilizing 'Boc Chemistry (Merrifield, 1963). Side chain protecting groups were as follows: Arg (Tos), His(Z), Glu(OcHex), Thr(Bzl), Tyr(2BrZ), Cys(Meb) and Ser(Bzl). The peptides were synthesized on MBHA resin (0.73 mmoles/g) and the synthesis carried out on an ABI 430A automatic peptide synthesizer with certain minor modifications on the standard protocol. Couplings were performed with DCC with the exemption of Asn, Gln and Arg which were coupled as their HOBt esther. Amino acid incorporations were monitored by ninhydrin test (Kaiser et al, 1970). The completed peptide resins were treated with liquid HF/dimethyl sulphide/p-cresol/p-thiocresol (90:6.2.2. vol/vol), at 0° C. for 1 hr. HF was removed and the resulted free peptides were solubilized in 10% aqueous acetic acid.

The crude peptides were purified by semipreparative RP HPLC on a C-18 column (16×250 mm). The peptides were eluted with a linear gradient of acetonitrile (15%→40%, in 50 min). The appropriate fractions were pooled and lyophilized. The purified peptides were characterized by amino acid composition and mass spectrometry. Peptide purities were above 96% (HPLC and CZE).

Reagents and Cell Culture Media. Tissue culture media and supplements were purchased from GIBCO (Grand Island, N.Y., USA). Triton X-100, PMSF and p-nitrophenyl-N-acetyl-β-D-glucosamine were from Sigma Chemical Co., (St. Louis, Mo.), EGTA and DMSO from Merck (Darmstadt, Germany). $DNP_{11}$-BSA was prepared by derivatization of BSA with 2,4-dinitro-benzene-sulfonic acid (Merck). Murine DNP-specific IgE class mAb $A_2$ (Rudolph et al, 1981) was grown as ascites in mice.

Cells. Rat mucosal mast cells, subline RBL-2H3 (Barsumian et al, 1981) were maintained in Eagle's MEM with Earle's salts supplemented by 10% FCS, 2 mM glutamine and antibiotics in a humidified atmosphere with 7% $CO_2$ at 37° C.

For the experiments, cells were harvested following 15 min incubation with 10 mM EDTA in MEM and maintained in Tyrode's buffer: 137 mM NaCl, 2.7 mM KCl, 1.8 mM $CaCl_{2\ 0.5}$ MM $MgCl_2$, 0.4 mM $NaH_2PO_4$, 5.6 mM glucose, 10 mM HEPES, 0.1% BSA, pH 7.4. Cell viability was assayed by Trypan blue dye exclusion and was invariably greater than 96%. Mouse bone marrow derived mast cells (BMMC) were generated by culturing bone marrow cells of Balb/c mice in IL-3 containing medium. Mouse fibrosarcoma cell line WEHI-164-13 were originally from Walter and Elisa Hall Institute in Melbourne, Australia. These cells are highly sensitive to TNF and therefore serve for the cytokine bioassay.

Secretory Response of Mast Cells. Mediator secretion by mast cells in response to stimulation by FcεRI clustering was monitored by measuring the activity of the granular enzyme β-hexosaminidase. DNP-specific murine IgE mAb, $A_2$ (3 μl ascites) was added to $10^6$ cells in 10 ml MEM and incubated in 96-well plates (100 μl suspension/well) for 2 h.

Then, monolayers were washed three times with Tyrode's buffer and stimulated with the antigen ($DNP_{11}$-BSA). To study the effect or peptides representing certain sequences of the complement-peptide C3a on the antigen-induced triggering, cells were pre-incubated with a range of these peptides for 5 min at room temperature before the addition of various concentrations of the antigen, $DNP_{11}$-BSA. Following incubation at 37° C. for 1 h, 20 μl of supernatants were taken and incubated with 50 μl of substrate solution (1.3 mg/ml p-nitrophenyl-N-acetyl-β-D-glucosamine in 0.1 M sodium citrate, pH 4.5) at 37° C. for 45 min. The reaction was terminated by the addition of 150 μl of 0.2 M glycine, pH 10.7, and the optical density of the samples was measured at 405 nm.

Results of one representative experiment out of four yielding similar results are presented as percent of the total cell content of the enzyme minus the basal secreted activity.

$^{45}Ca^{2+}$ Uptake Measurements. $^{45}Ca^{2+}$ uptake experiments are performed at 35° C. (hot room). Cell monolayers are washed with prewarmed Tyrode's buffer several times to remove unbound IgE and incubated with the inhibitory peptide in 950 μl Tyrode's for 15 minutes or as otherwise specified. $^{45}Ca^{2+}$ uptake is initiated by addition of $^{45}CaCl_2$ (5 μCi) with or without antigen ($DNP_{10}$-BSA, 2 μg) in 50 μl followed by a brief agitation. Plates are left unstirred throughout the uptake period. $^{45}Ca^{2+}$ influx is typically stopped by suction of the buffer and by rapid washing of the plates three times with a stop solution (135 mM choline chloride, 50 μM DNP-glycine, 10 mM HEPES/K, pH=7.2). The latter is designed to abrogate $Ca^{2+}$ losses through the sodium-calcium exchanger or through any potential pathway which might be activated by receptor aggregation. Washing is completed within 15–20 seconds. Cells are disrupted by 1 ml water (left for 30 min) and aliquots counted for $^{45}Ca$ radioactivity.

Determination of TNF secretion by mast cells. RBL-2H3 cells sensitized with DNP-specific A2 IgE are plated in 96-well plates. Following 2 hours incubation at 37° C. and washing off non-adherent cells, medium or the inhibitory peptides are added to the samples in various dilutions. After 5 min at 20° C. the antigen, DNP-BSA is added to the cells. Culture supernatants for the measurement of TNF are collected after 20 hours.

For the determination of TNF-release, the WEHI-164-13 line is used. To WEHI-164-13 cells suspended at $3\times10^5$ cells/ml, actinomycin is added at the concentration of 2 μg/ml followed by the distribution of the cells in 96-well plates in 100 μl. 50 μl of the supernatants of RBL-2H3 cells are added in triplicates to the TNF-sensitive cells. After culturing for 24 hours at 37° C., 50 μl of 5 mg/ml MTT (3-[4,5-dimethylthiazol-2yl]2,5 diphenyltetrazolium bromide is added to the cultures' wells. Following 6 hours, 100 μl of 10% SDS in 0.01N HCl is added to the samples and the OD is measured at 490 nm. The TNF-activity is calculated and expressed in units/ml referring to the standard curve prepared using serial dilutions of recombinant TNF (Sigma). Background values of unstimulated cells are subtracted and standard errors of results are calculated.

$Ca^{2+}$ Mobilization Assay. IgE-sensiLized mast cells at $5\times10^6$ cells/ml are loaded with 5 μM fluo-3-AM indicator (Molecular Probes, Oragon, U.S.A.) and 30 μg/ml Pluronic F-127 for 30 min at 37° C. in RPMI medium. The cells are diluted 10-times with the medium and incubated for another 30 min at 37° C., then washed, resuspended at $5\times10^5$ cells/ml and labeled with 7-AAD to exclude dead cells. Dilutions of the inhibitory peptides are added to the cells at various concentrations and, after 5 min at 20° C., antigen ($DNP_{11}$-BSA) is added to the cells. Alterations of cytosolic free calcium ion concentration are detected as shifts of the mean fluorescence intensity of intracytoplasmic fluo-3 calcium indicator. Time course of the change of mean fluorescence are calculated by lysis II software (BectonDickinson).

The GP Model of Allergic Reaction. Guinea pigs (GPs), weighing 350–400 g (from Charles River, GB) were sensitized to rabbit anti-chicken egg albumin (Sigma) by i.p. injection (0.6 mg/kg, using a solution of 1.5 mg/ml in DDW). Twenty-four hours following sensitization, GPs were challenged with inhaled aerosol of chicken ovalbumin (Sigma). The aerosol was generated from an aqueous solution of 25 mg/ml and aerosolized with air 24 l/min. Exposure duration was 1–3 min, according to the required dose. The calculated dose was 70, 105 and 210 μg of inhaled OA/GP for 1, 1.5 and 3 minutes of exposure respectively. During the challenge the GPs were restrained in plethysmographs and their tidal volume, minute volume and respiration rate parameters were monitored. The GPs that received pretreatment with tire mast cell inhibitor C3a9 treated with aerosolized C3a9 peptide (a solution of 0.25 mg/ml, aerosolized with air 24 l/min and treated for 10 min.). The treatment ended 5 min before the challenge with OA. It is estimated that under these conditions each GP inhaled about 7 μg of the peptide. Respiratory parameters of the animals were further monitored for 10 min post challenge.

Bronchoalveolar Lavage (BAL). Twenty-four hours post exposure, GPs were anesthetized (1 ml of Nembutal solution per GP), and their lungs were washed with 2×3 ml of saline. The collected BAL was centrifuged for 10 min at 15000 rpm at 4° C. The supernatants were separated for future assays. The cell pellet of each BAL was re-suspended in 1 ml of saline and 20 μl were air dried on a glass slide. The slides were then fixed for 30 min in methanol, stained with Giemza stain for 60 min, washed in DDW, air dried and covered using glycerol—gelatin. Slides were coded for a blind unbiased cell count. Since eosinophils were aggregated in several fields and were not uniformly scattered on the slide, the common method of a random cell-count in a number of sub-fields might lead to biased estimates and was not used. Instead, the percentage of eosinophils in the entire slide was estimated. Each slide underwent two separate evaluations, and the results are given as an average of these two estimates.

Example 1

Preparation of Peptides C3a2, C3a2-R and rC3a2

C3a2. The heneicosapeptide amide was built step by step on methyl-benzhydrylamine resin containing 0.73 meq $NH_2$/g in a reaction vessel for automated solid-phase synthesis starting with Boc-Arg(Tos) in accordance with the procedures set forth below. The methyl-benzhydrylamine resin (138 mg in hydrochloride form, about 0.1 mmol), after neutralization with DIEA in $CH^2Cl_2$, was coupled sequentially with 10 molar excess of protected amino acids in accordance with the schedule as follows:

1) Heat TFA for 5 min
2) First drain
3) DMF flow-wash for 40 sec
4) 20% DIEA in DMF for 1 min
5) DMF flow-wash for 40 sec
6) Second drain
7) Coupling period
8) DMF flow-wash for 40 sec
9) Third drain Steps 1–9 complete a coupling cycle for one amino acid. Thus the resin was treated during successive coupling cycles with Boc-Ala, Boc-Leu, Boc-Gly,-Boc-Leu, Boc-His(Z), Boc-Ser(Bzl), Boc-Ala, Boc-Arg(Tos), Boc-Ala, Boc-His (Z), Boc-Gln, Boc-Arg(Tos), Boc-Arg(Tos), Boc-Leu, Boc-Glu(OcHex), Boc-Thr(Bzl), Boc-Ile, Boc-Tyr(2BrZ), Boc-Asn and Boc-Cys(Meb) (1.0 mmol of each). The peptide resin obtained 485 mg was treated with 0.6 ml dimethyl sulphide, 0.2 ml p-cresol, 0.2 ml p-thiocresol and 9 ml HF at 0° C. for 45 min. After elimination of HF under high vacuum, the remainder peptide resin was washed with dry diethyl etiher. The peptide was then extracted with 10% aqueous acetic acid, separated from the resin by filtration and lyophilized. Yield: 190 mg.

The crude peptide C3a2 (80 mg) was purified using a KNAUER semipreparative HPLC system. Separations were achieved on a 16×250 mm column packed with C18 silica gel (300 angstrom pore size, 25–40 μm particle size) with solvents A: 0.1% aqueous TFA and B: 0.1% TFA in 80% aqueous MeCN (referred to as system i in the following) using a gradient of 15–40% B in 50 min. The column eluate was monitored at 226 nm. The peptide thus obtained (12 mg) was judged to be substantially (more than 96%) pure by using a Hewlett-Packard Model HP-1050 liquid chromatograph. The peptides were chromatographed on a 4.6×250 mm, 5 μC18 column at a flow rate of 1.0 ml/min with solvent system i in a linear gradient mode (24–39% B in 15 min). Retention time for the heneicosapeptide was 8.12 min.

Amino Acid Analysis: Asp: 1.12, Glu: 2.14, Ser: 0.92, His: 1.90, Gly: 1.24, Ala: 3.03, Arg: 4.01, Tyr: 0.78, Ile: 1.00, Leu: 3.04. MS: 2463.85 (caic.), 2464.4 (found).

TABLE 1

Codes, Inhibitory Capacity, Sequences and Properties of Peptides

| Code | Concentration ranges causing 50% inhibition | Peptide Sequence | Mass Spectra calc. | found | SEQ ID NO: |
|---|---|---|---|---|---|
| C3a1 | 0 | SVQLTEKRMDKVGKYPKELR | 2404.88 | 2406.5 | 1 (residues 1–20) |
| C3a2 | 100–150 μg/ml | CNYITELRRQHARASHLGLAR | 2464.85 | 2465.6 | 1 (residues 57–77) |
| C3a2-R | 100–150 μg/ml | CNYITELRRQHARASHLGLA | 2308.66 | 2309.0 | 1 (residues 57–76) |
| rC3a2 | 120–180 μg/ml | CNYITKLREQHRRDHVLGLAR | 2578.01 | 2578.2 | 19 |
| C3a3 | 0 | RQHARASHLGLAR | 1471.70 | 1474.4 | 1 (residues 65–77) |
| C3a4 | 0 | KVFLDCCNYITELR | 1716.05 | 1716.5 | 1 (residues 51–64) |
| C3a5 | 0 | KKVFLDCCNYITELRRQHAR | 2492.96 | 2493.0 | 1 (residues 50–69) |
| C3a6 | 300–600 μg/ml | KVFLDAANYITELRR | 1808.11 | 1808.8 | 23 |
| C3a7 | 30–60 μg/ml | CCNYITELR | 1113.33 | 1113.8 | 1 (residues 56–64) |
| C3a8 | 0 | KKVFLDR | 904.12 | 903.6 | 24 |
| C3a9 | 5–10 μg/ml | DCCNYITR | 986.14 | 86.2 | 20 |
| C3a10 | 0 | RRCCNYITRR | 1339.61 | 1340.1 | 25 |
| C3a11 | 120–180 μg/ml | DSSNYIR | 852.90 | 853.6 | 21 |
| C3a12 | 0 | DCCNYG | 673.73 | 674.0 | 26 |
| C3a13 | 0 | CCNYG | 558.64 | 559.0 | 22 |
| C3a14-P | 100–150 μg/ml | DSSNYITR | | | 27 |

The peptides of the invention C3a2, C3a2-R, rC3a2, C3a4, C3a5, C3a6, C3a7, C3a8, C3a9, C3a10, C3a11, C3a and C3a14-P and the comparison peptides C3a1 and C3a3 listed in Table 1 were synthesized using the same technique.

Example 2

Inhibition of Antigen-Induced Secretion by RBL-2H3 Cells

In order to examine the inhibition of antigen-induced degranulation by the C-terminal and N-terminal sequences of C3a, RBL-2H3 cells were saturated with the DNP-specific monoclonal IgE, mAb $A_2$, pre-incubated with concentrations of peptides C3a1 or C3a2 ranging from 500 μg/ml to 16 μg/ml (5 min, room temperature), then subsequently stimulated by the addition of the antigen ($DNP_{11}$-BSA) at 5 ng/ml. The effect of the highest concentration of the peptide alone is also shown in FIG. 1. Degranulation of the cells was monitored by measuring the activity of the enzyme β-hexosaminidase released into the supernatants after stimulation for 1 h at 37° C. and are presented as net percentages of the cells' total β-hexosaminidase activity.

The results are shown in FIG. 1 wherein columns 1–6 represent peptide concentrations: 500, 250, 125, 62.5, 32, and 16 μg/ml; column 7 represents 500 μg/ml peptide (C3a1 or C3a2) alone, and column 8 represents antigen alone.

As shown in FIG. 1, the C-terminal 21-mer peptide of human C3a (C3a2) inhibited in a dose-dependent manner the antigen-induced release of the granular enzyme β-hexosaminidase secretion by RBL-2H3 cells. The inhibitory concentration of the peptide ranged from 25 μg/ml to 500 μg/ml. No secretory response was observed when only the peptide was added to the cells in the same range of concentrations. The effect of the highest concentration of the peptide alone is also shown.

The peptides C3a9, C3a11 and C3a13 were tested and shown to inhibit IgE-dependent degranulation of RBL-2H3 cells to a similar extent as did C3a2.

The N-terminal peptide (C3a1) containing 20 amino acid residues of human C3a had no effect at all.

Example 3

Figure 2A:
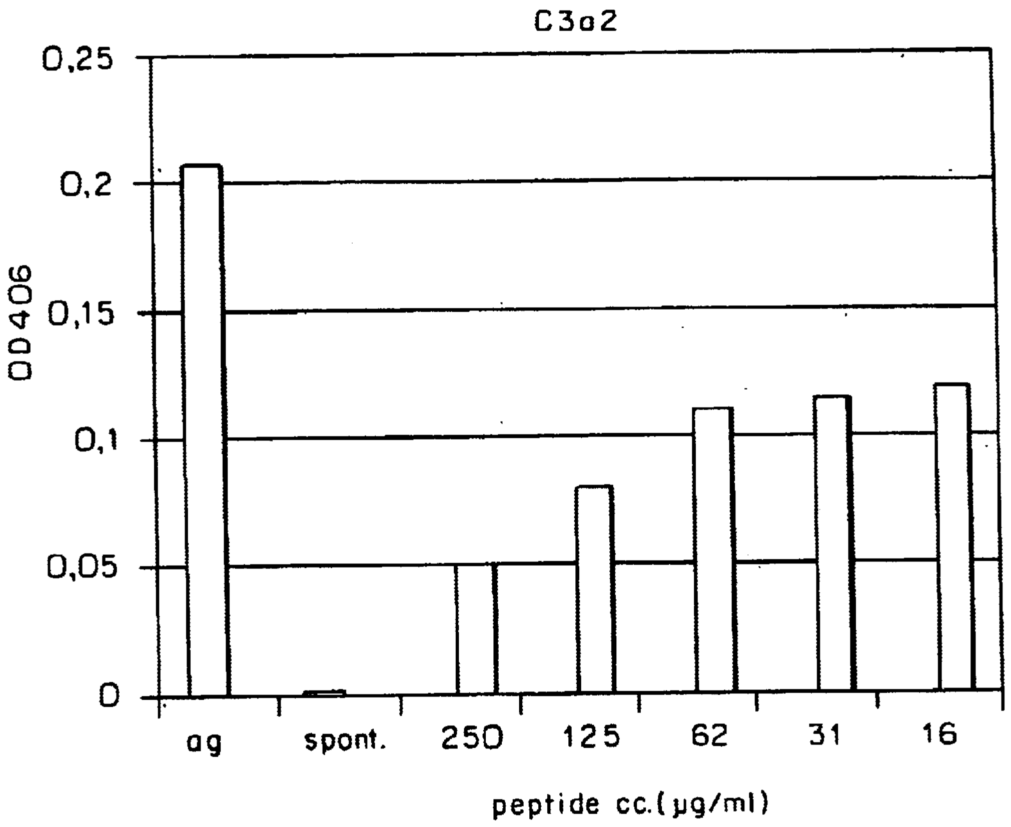
FIGS. 2A–2E are graphs showing the effect of C3a2 (FIG. 2A), C3a7 (FIG. 2B), C3a9 (FIG. 2C), C3a11 (FIG. 2D), and C3a14-P (FIG. 2E) on the IgE-mediated enzyme release of RBL-2H3 cells.
Figure 2B:
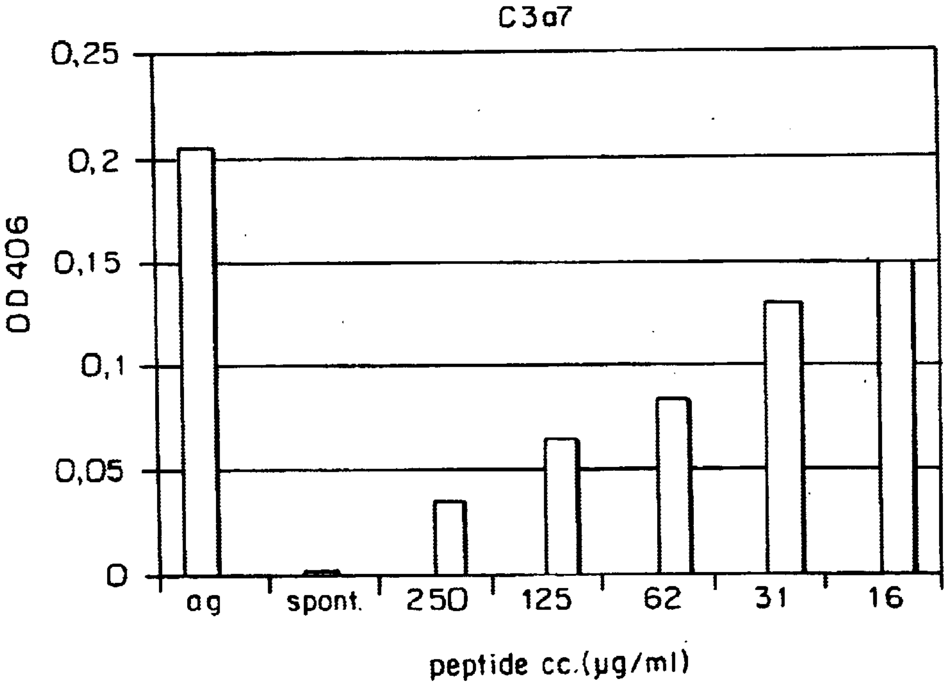
Figure 2C:
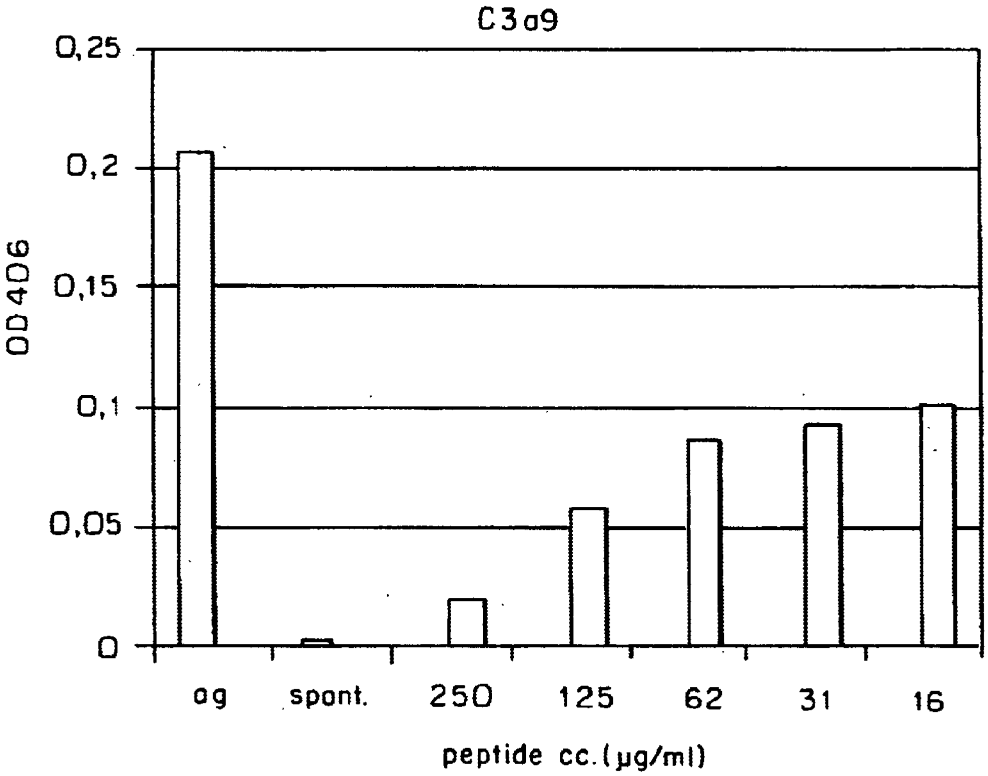
Figure 2D:
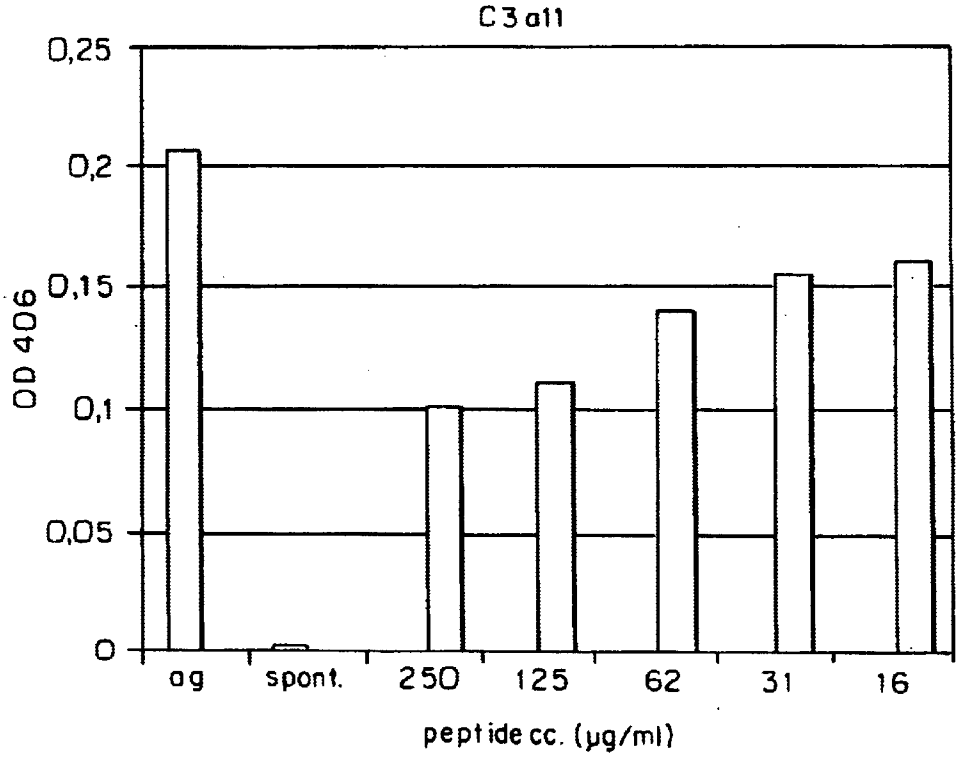
Figure 2E:
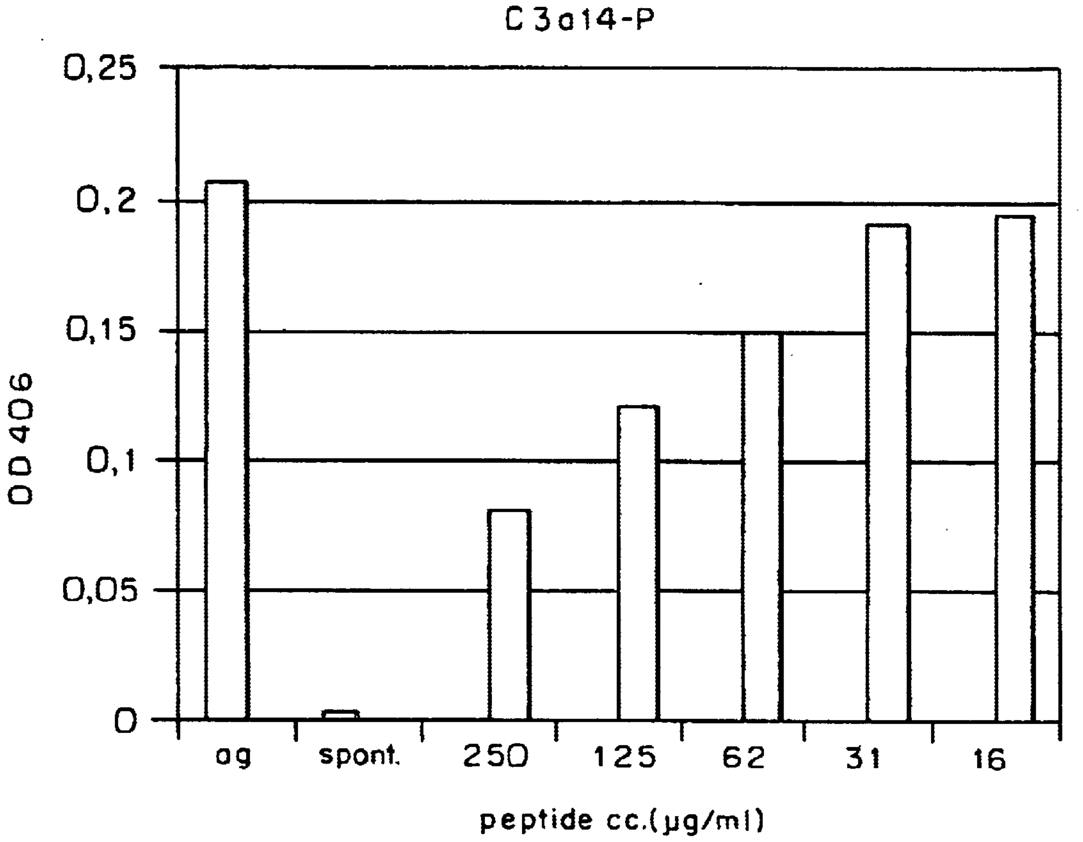

The effect of Various Peptides on the IgE-Mediated Enzyme-Release of RBL-2H3 Cells RBL-2H3 cells were sensitized with DNP-specific IgE followed by incubation with the peptides at room temperature for 5 min. Then the antigen $DNP_{11}$-BSA was added to the cells and their secretory response was monitored by measuring the activity of the granular enzyme β-hexosaminidase. Peptides C3a2 (FIG. 2A), C3a7 (FIG. 2B), C3a9 (FIG. 2C), C3a11 (FIG. 2D) and C3a14-P (FIG. 2E) were used at concentrations ranging between 500 and 16 μM as marked. The first column represents antigen alone, and the second column represents the peptide alone. The Y-axis is the OD reading.

Example 4

The Effect of Various Peptides on the IgE-Mediated Enzyme-Release of Bone Marrow Derived Mast Cells (BMMC)

Figure 3:
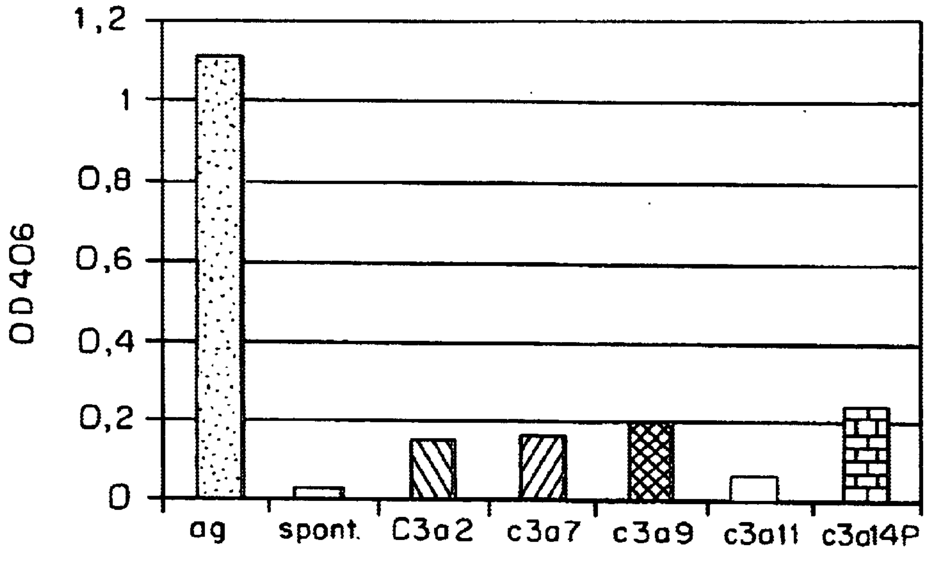
FIG. 3 is a graph showing the effect of various peptides on the IgE-mediated enzyme release of bone marrow derived mast cells (BMMC).

BMMC were generated by culturing bone marrow cells of Balb/c mice for 4–5 weeks in IL-3 containing medium RPMI. Maturation to mucosal type mast cells was tested by their capacity to bind FITC-labeled IgE. Treatment of the IgE-sensitized cells with the peptides was carried out as described above and degranulation of the cells was monitored by measuring released P-hexosaminidase. Peptides C3a2, C3a7, C3a9, C3a11 and C3a14-P were used at the concentration of 150 μM (FIG. 3).

Example 5

Figure 4A:
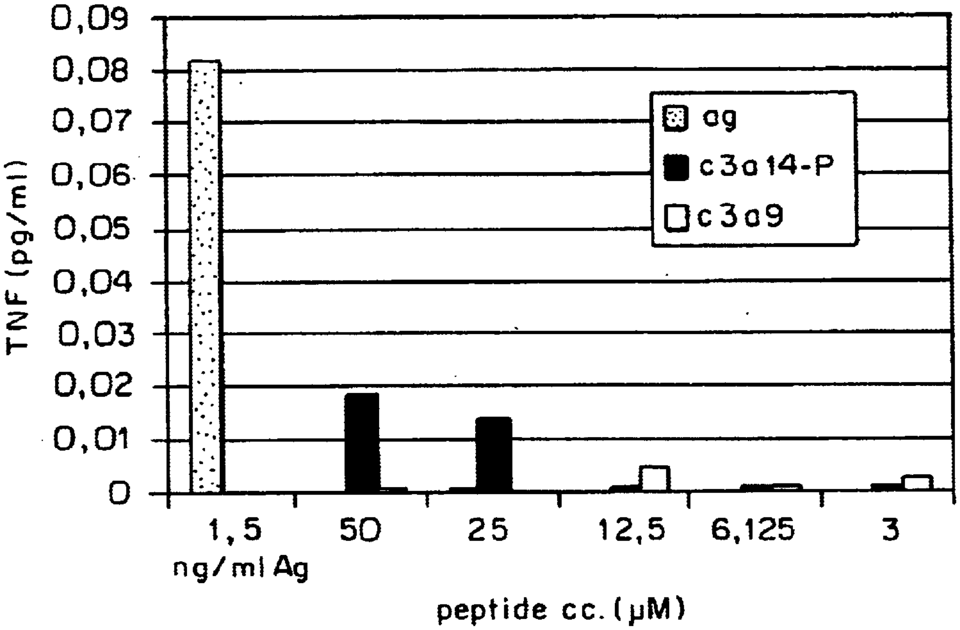
FIGS. 4A–4B are graphs showing the inhibitory effect of various peptides on TNF release by RBL-2H3 cells, measured after two hours.
Figure 4B:
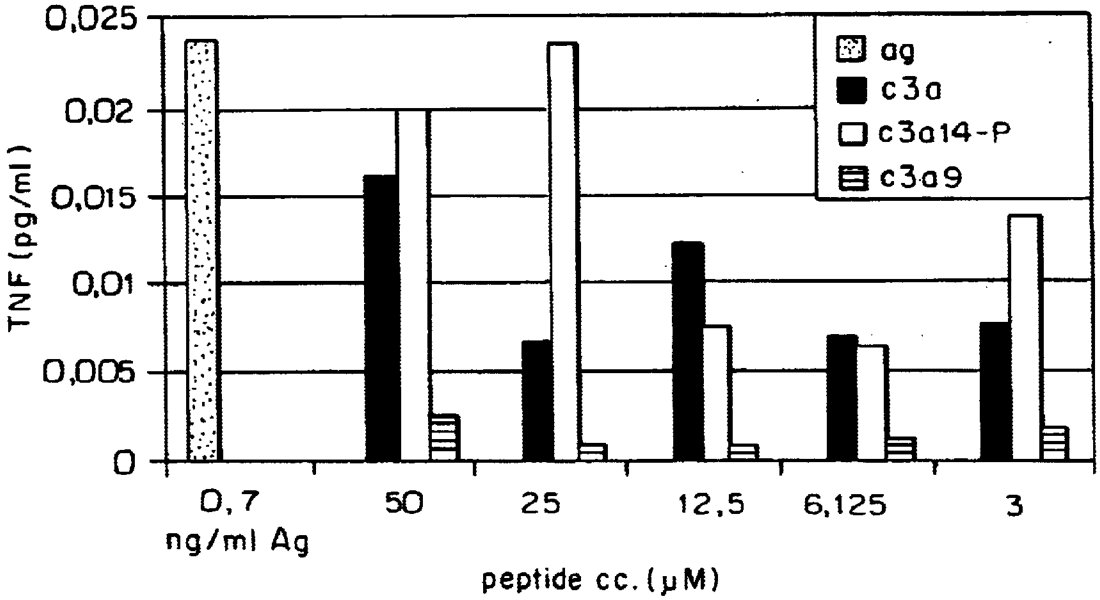

The Effect of Various Peptides on the IgE-Mediated TNF-Release of RBL-2H3 cells RBL-2H3 cells were sensitized with DNP-specific IgE followed by incubation with the peptides at room temperature for 5 min. Then the antigen $DNP_{11}$-BSA was added to the cells in two concentrations (1.5 and 0.7 ng/ml) and samples of supernatants were taken after 2 hours. Secreted TNF was measured by bioassay, using WEHI 164 cells. Peptides C3a9 and C3a14-P were used at the concentrations ranging between 50 and 3 μM. At the lower antigen dose, C3a was also included. The results at 1.5 ng/ml are shown in FIG. 4A. The results at 0.7 ng/ml are shown in FIG. 4B.

Example 6

Figure 5A:
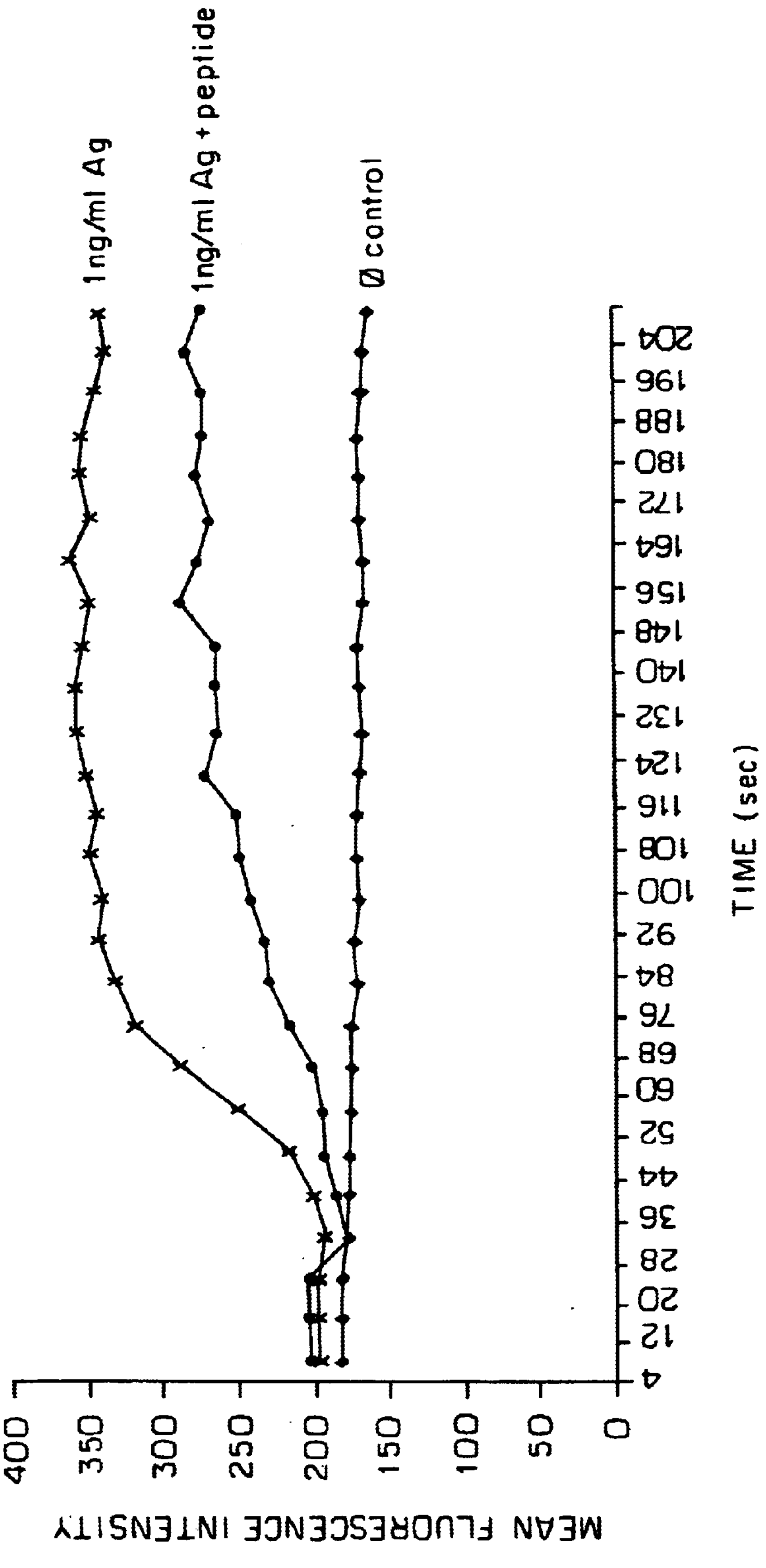
FIGS. 5A–5B are graphs showing the IgE-mediated Ca influx of RBL-2H3 cells to antigen stimulus, alone and in the presence of peptide C3a14-P (FIG. 5A) or C3a9 (FIG. 5B).
Figure 5B:
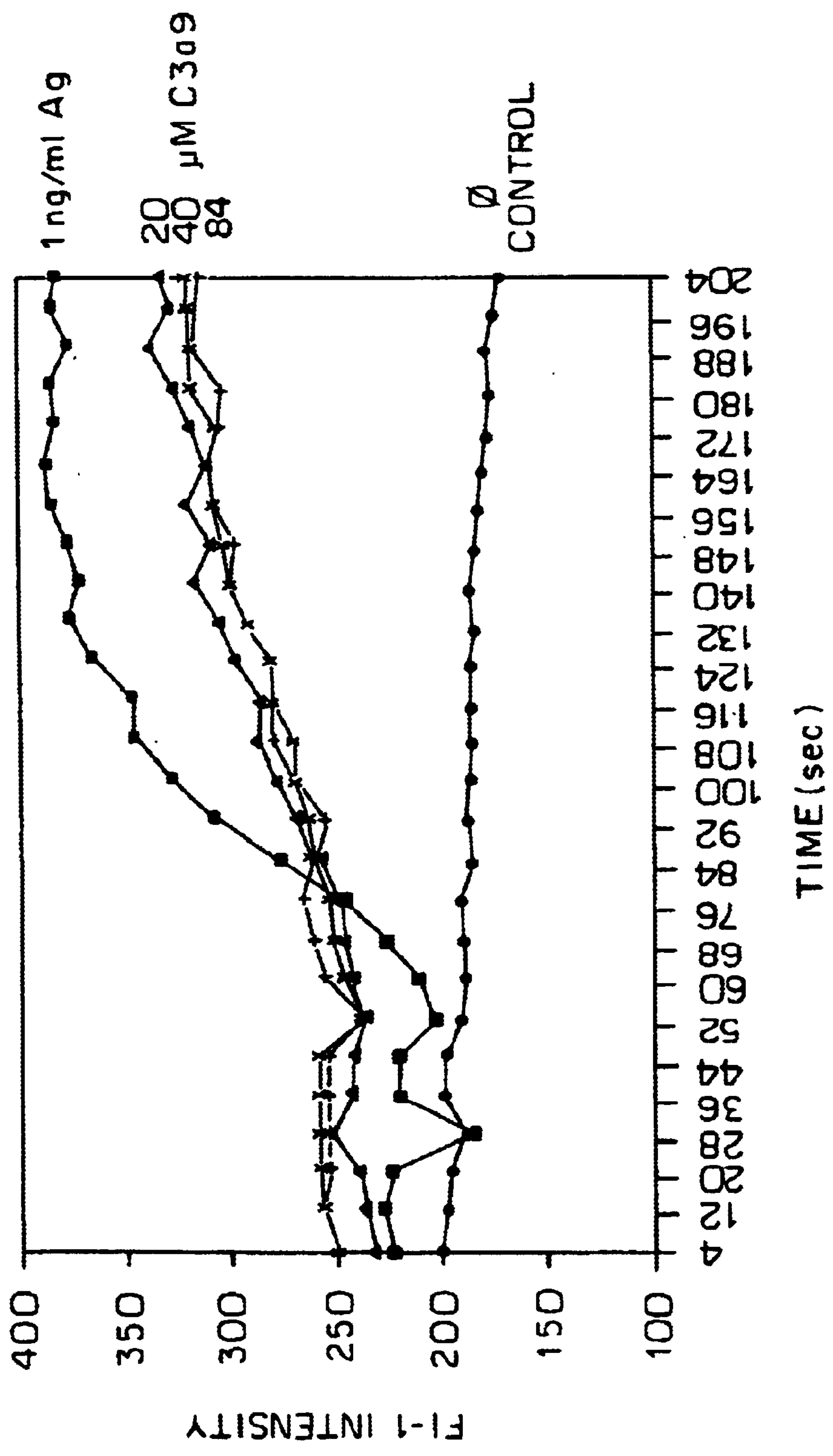

Effect of Various Peptides on Free Cytosolic $Ca^{2+}$-ion Concentrations $[Ca^{2+}]_i$ in RBL-2H3 Cells RBL-2H3 cells pre-incubated with the murine, DNP-specific IgE fluro-3 acetoxymethyl ester (dissolved in DMSO) at 37° C. for 30 min. After washing, aliquots of cells were incubated with the peptides C3a9 and C3a14-P at room temperature for 5 min, followed by the addition of the antigen. Fluorescence intensity of the cells was monitored by FACSCalibur instrument. Peptide C3a14-P was used at the concentration of 50 AM (FIG. 5A); C3a9 was used at 20, 40 and 80 μM (FIG. 5B).

Example 7

Binding of Various Peptides to RBL-2H3 Cells and to BMMC

Flow cytometry measurement showed binding of FITC-15 labeled C3a14-P to RBL-2H3 cells and BMMC and resonance energy transfer between bound peptide and bound IgE(results not shown). This supports proximity between the FcεR (IgE receptor) and the peptide.

Example 8

Effect of Various Peptides on the Fluorescence Resonance Energy Transfer (FRET) between FTTC-IgE and TRITC-IgE on RBL-2H3 Cells The Forster-type resonance energy transfer between FITC-IgE and TRITC-IgE targeting FcεRI molecules on RBL-2H3 cells was measured (at 1:1 donor-acceptor ratio) by flow cytometry using a BectonDickinson FACStar Plus flow cytometer. The energy transfer efficiency values proportional to the extent proximity were determined on a cell by cell basis from 20,000 cells/sample, and the mean values are listed in Table 2. (The typical S.D. of these measurements was ±0.8%.)

TABLE 2

The Efficiency of FITC-IgE and TRITC-IgE Homo-FRET on Control RBL-2H3 Cells: E:30.1 ± 7% (n = 4)

| Peptide | dE %* Dose 1 | Dose 2 |
|---|---|---|
| C3a | −80 (30 μM) | −115 (70 μM) |
| C3a2 | −101 (110 μM) | −130 (270 μM) |
| C3a5 | −65 (110 μM) | −78 (270 μM) |
| C3a9 | −64 (290 μM) | −67 (670 μM) |
| C3a14-P | −72 (250 μM) | −97 (630 μM) |

*dE = (E/E [control] − 1) × 100 (%). −100% or greater change means that the FRET-histogram mean is close to 0, i.e., no homotransfer is detectable.

Example 9

Dose-Dependent Binding of FITC-Labeled C3a14-P to RBL-2H3 Cells

RBL-2H3 cells were incubated with the peptide at various concentrations and binding was measured after washing the cells. The results in Table 3 show that there is specific binding, but no saturation is reached.

TABLE 3

| Peptide Dose ($\mu$M) | Fluorescence Mean (w/o background) |
|---|---|
| 250 | 25 |
| 510 | 74 |
| 630 | 157 |

Example 10

FRET between C3a14-P-FTTC and IgE-TRITC on RBL-2H3 Cells

The data in Table 4 show that the distance between the peptide and rhodamine-groups on the IgE-molecule is app. 9 nm, which is very little considering the size of FcεRI and suggests that the binding sites for the peptide and IgE are very close.

TABLE 4

| Cells Incubated with Various Amounts C3a14-P-FITC | FRET Efficiency E (%) |
|---|---|
| 20 | 33 |
| 40 | 17 |
| 60 | 9 |

Example 11

Modulation of Anaphylactic Shock by C3a9 in Ovalbumin-Sensitized Guinea Pig Model Anaphylactic shock, induced in sensitized guinea pigs (GPs) by ovalbumin (OA), was shown previously to lead to massive contraction of airways and even death. This reaction is a result of activation of mast cells in response to the challenge, leading to a release of inflammatory mediators and extensive infiltration of eosinophils.

In this example, sensitized GPs were challenged with OA while respiratory parameters and survival rate were monitored. Eosinophilic infiltration was observed in the surviving GPs. The results revealed that aerosolized OA (about 105 $\mu$g OA inhaled per GP) killed 87% of the challenged GPs and led to around 10-fold increase in eosinophils among the surviving animals. Pretreatment of the GPs with aerosolized complement C3a9 (about 7 $\mu$g/GP), a known inhibitor of the IgE mediated activation of mucosal mast cells, blocked the monitored respiratory distress, reduced the incidence of death and prevented almost completely the infiltration of eosinophils.

Allergic reaction is strongly dependent on activation of mast cells and their secretory response. Activation of these cells is followed by release of histamine and other inflammatory mediators including proteases, leukotrienes and various cytokines. These secretory responses trigger airway contraction (Turner, 1965) and infiltration of eosinophils into the bronchoalveolar area (Gulbenkian et al, 1990). In a full blown allergic reaction, airway contraction may lead to acute bronchoconstriction and death, which is termed anaphylactic shock. The infiltration of eosinophils in response to mast cell activation usually starts 3 hours following exposure, peaks at 24 h and lasts up to 7 days (Underwood et al, 2000).

In this example, the effect of C3a9 was tested for its ability to reduce the anaphylactic shock induced by OA challenge in sensitized guinea pigs. Treating sensitized GPs with C3a9, prior to the challenge with OA, and measuring the effect of the treatment on survival and respiratory distress was used for this purpose, as well as monitoring of the eosinophilic infiltration in the bronchoalveolar lavage (BAL).

The Effect of C3a9 on Allergic Response. Three experimental groups were used in this study as described in Table 5. Eight GPs were tested in each group.

TABLE 5

Design of the Experimental Groups

| Treatment/group # | 1 | 2 | 3 |
|---|---|---|---|
| Sensitization (i.p.)* | + | + | − |
| Treatment with aerosolized C3a9** | + | − | − |
| Challenge with aerosolized OA*** | + | + | + |

*Sensitization with anti-ovalbumin (rabbit) 0.6 mg/kg
**Treatment with inhaled aerosol of C3a9 in water ~7 $\mu$g/GP during 10 min
***Challenge with inhaled aerosol of ovalbumin ~105 $\mu$g/GP during 1.5 min Additional 2 groups of 4 GPs (groups 4 and 5) were exposed to the challenge for 1 min and 3 min, respectively.

Since the concentration of OA was constant in all the experiments, the inhaled doses were 70 $\mu$g OA/GP and 210 microgram OA/GP, for 1 and 3 minutes exposure, respectively.

Figure 7A:
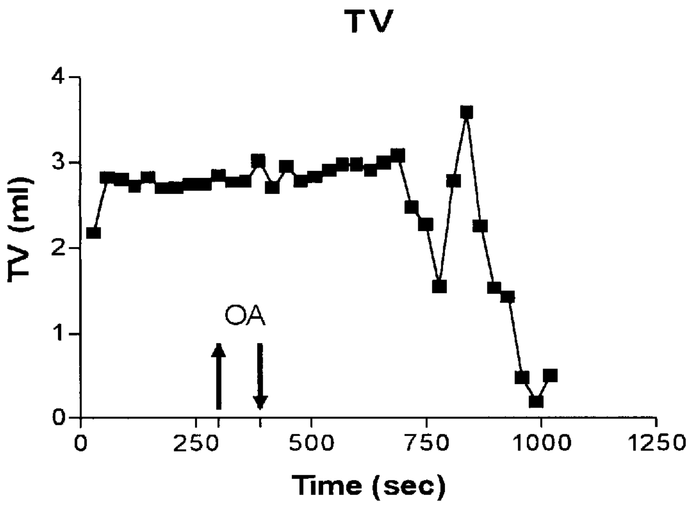
FIGS. 7A–7C are graphs showing the monitoring of tidal volume (TV) (FIG. 7A), respiration rate (RR) (FIG. 7B) and minute volume (MV) (FIG. 7C) in the sensitized OA-challenged group (Group 2). The arrows indicate the beginning and the end of exposure to OA aerosol.
Figure 7B:
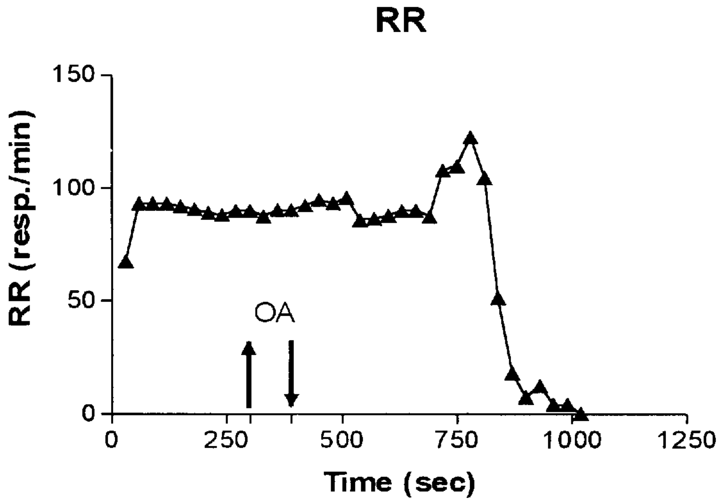
Figure 7C:
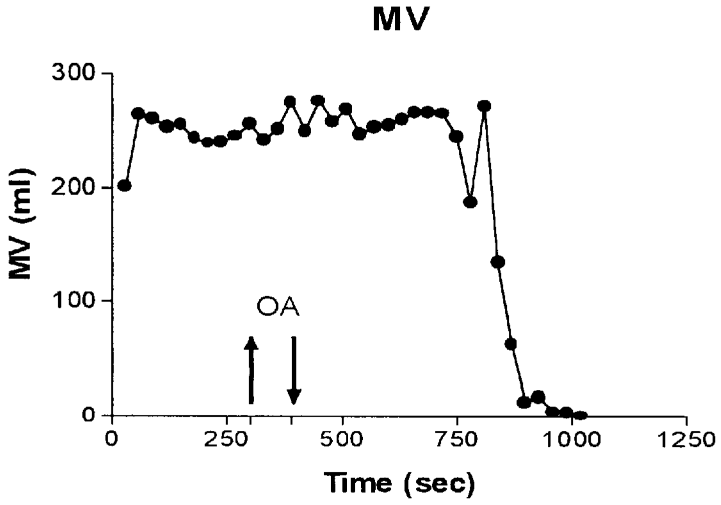

GPs sensitized with anti-chicken OA and challenged with OA 24 hours following sensitization, responded within 4–5 minutes by developing a severe bronchoconstriction, as demonstrated in respiratory parameters (FIG. 7). Death occurred in 7 of 8 sensitized GPs immediately following the onset of distress symptoms and within 10 minutes of the challenge.

Although some of the surviving GPs showed signs of respiratory distress, their recovery was fast and they regained normal respiratory parameters within 5–10 minutes after the onset of respiratory distress.

Figure 6A:
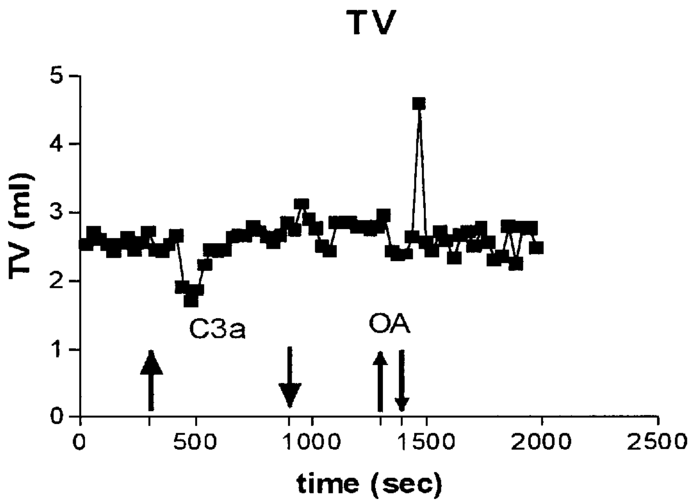
FIGS. 6A–6C are graphs showing the monitoring of tidal volume (TV) (FIG. 6A), respiration rate (RR) (FIG. 6B), and minute volume (MV) (FIG. 6C) in the sensitized, C3a9-treated group (Group 1). The large arrows indicate the beginning and the end of the treatment of C3a9 aerosol, while the small arrows indicate the exposure to OA aerosol.
Figure 6B:
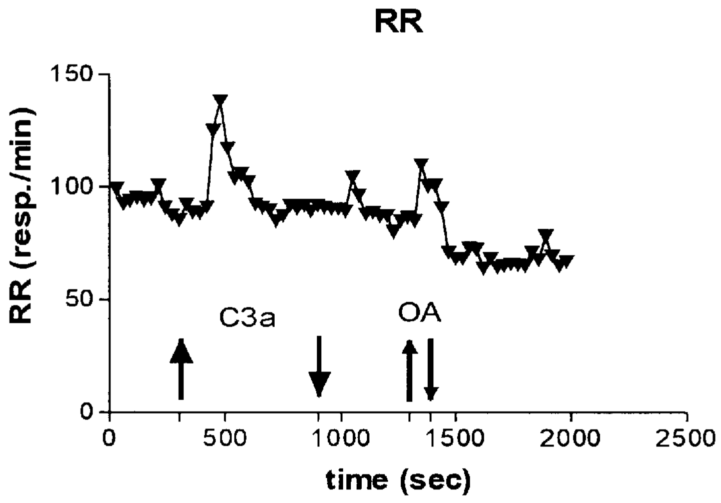
Figure 6C:
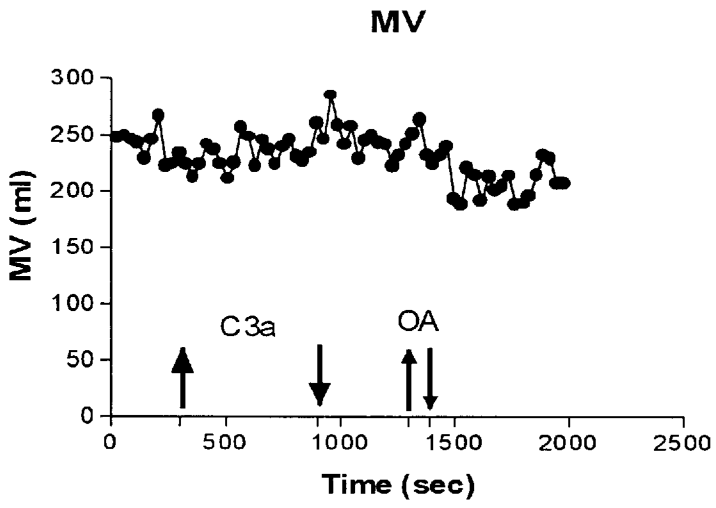
Figure 8A:
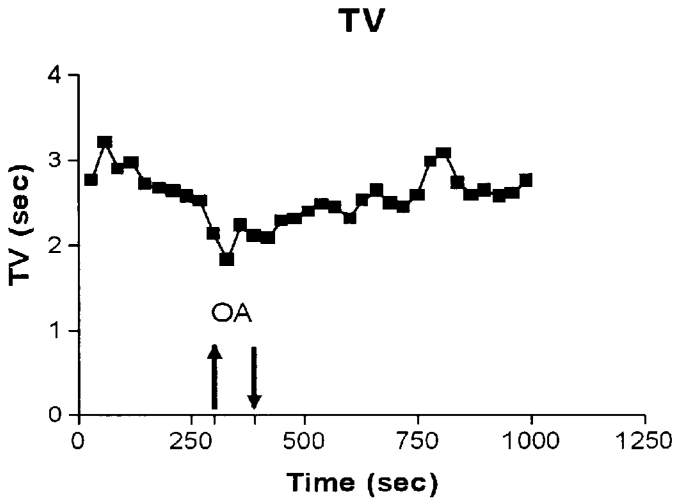
FIGS. 8A–8C are graphs showing the monitoring of tidal volume (TV) (FIG. 8A), respiration rate (RR) (FIG. 8B) and minute volume (MV) (FIG. 8C) in the non-sensitized OA-challenged group (Group 3). The arrows indicate the beginning and the end of exposure to OA aerosol.
Figure 8B:
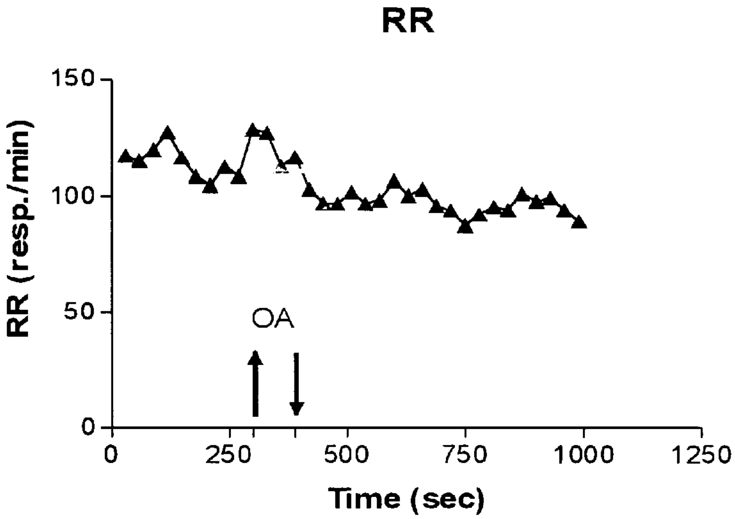
Figure 8C:
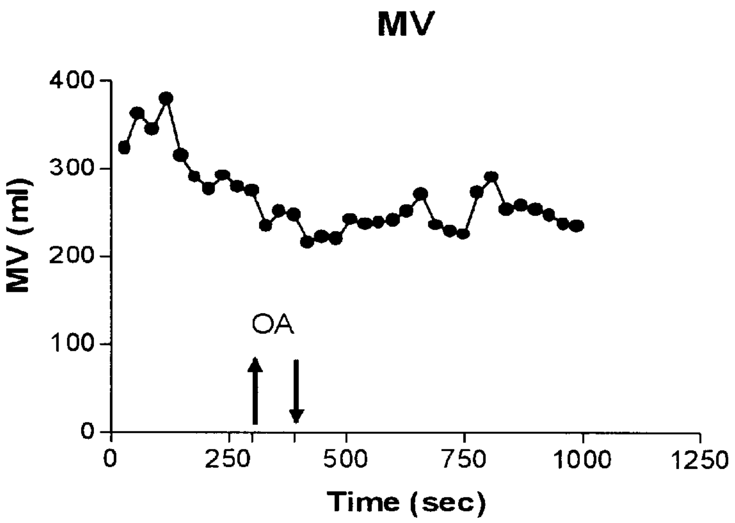

Treatment with C3a9 prior to the challenge, in sensitized GPs, reduced the number of GPs that developed symtoms of respiratory distress and reduced the incidence of death 2 out of 8 GPs (FIG. 6 and Table 6). In animals that were not sensitized 24 hours prior to the challenge, there were neither symptoms of respiratory distress nor death (FIG. 8). The survival ratios of the different groups are summarized in Table 6.

TABLE 6

Incidence of Death among the Various Experimental Groups

| Group # | Treatment group | Incidence of Death |
|---|---|---|
| 1 | Sensitized, treated and challenged for 1.5 min | 2/8 |
| 2 | Sensitized and challenged for 1.5 min | 7/8 |
| 3 | Challenged only for 1.5 min | 0/8 |
| 4 | Sensitized and challenged for 1 min | 1/4 |
| 5 | Sensitized and challenged for 3 min | 2/4 |

Transient changes were observed (mainly in the respiratory rate) when the GPs responded to either the aerosol of C3a9 or of OA. These transient effects were presumed to be a result of the changes in humidity. Except for these transient changes in respiratory parameters, GPs were not affected by the treatment with C3a9.

The respiratory effects of the exposure to OA was not immediate but delayed, as in classical allergic responses, and started 2–3 minutes following termination of the challenge (FIG. 7).

FIGS. 6–8 represent averages of four animals in each group; however, it should be noted that the variations between animals within each group were insignificant.

Figure 9:
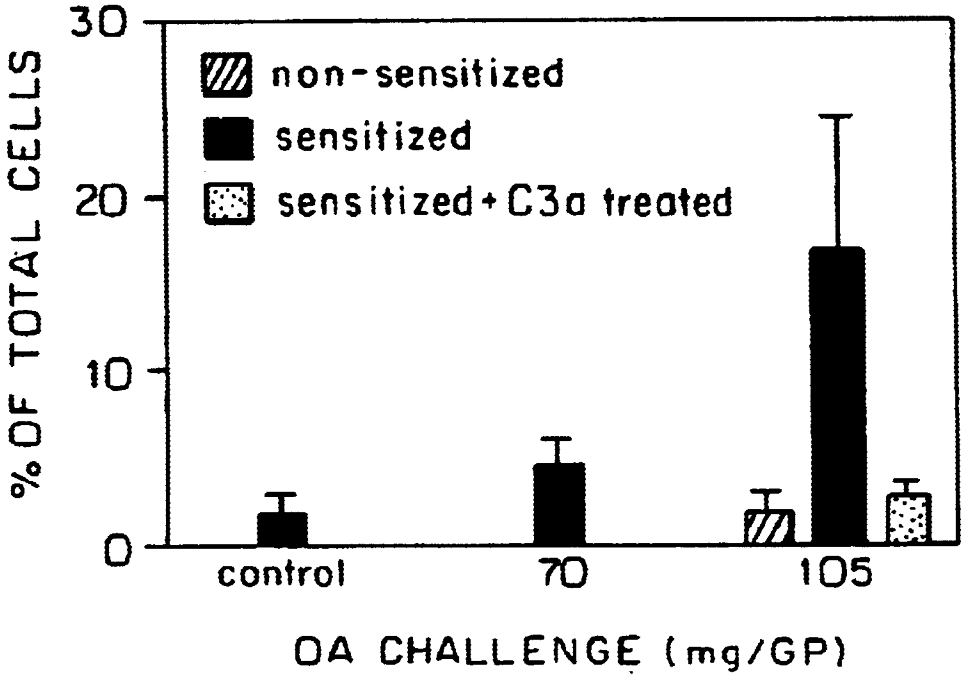
FIG. 9 is a graph showing the percentage of eosinophils in BAL of OA challenged, non-sensitized (striped), sensitized (black) and treated with C3a9 (check) GPs.

The Effect of C3a9 on Eosinophils in BAL. BAL was performed on the surviving GPs 24 hours post challenge (see methods). The percentage of eosinophils in the BAL was blindly evaluated twice for each BAL. In GPs exposed to the higher doses of OA (105 and 210 μg), anaphylactic challenge was shown to induce a 10-fold increase in eosinophil count in the BAL, as compared to the count in the non-sensitized control group (Table 7 and FIG. 9). These results are in accordance with previous studies showing a similar increase in eosinophils in BAL following sensitization and challenge (Underwood et al, 2000). Because of the small number of surviving animals, the present inventors combined three surviving GPs: one GP exposed to 105 μg of OA, and two exposed to 210 μg of OA in the same group (Table 7). The eosinophils count in the GPs treated with C3a9, that survived the challenge, was reduced almost to the levels of control (1.7-fold above that of the non-sensitized GPs). A dose-response relationship was observed between the percentage of eosinophils in the BAL and the dose of OA used for challenge (Table 7, FIG. 9).

TABLE 7

Percentage of Eosinophils of the Total Number of Cells in BAL

| Group # | Treatment | Eosinophils (%) Av. ± SD |
|---|---|---|
| 1 | Sensitized, C3a9 treated exposed to 105 μg OA/GP (n = 6) | 2.7 ± 0.6 |
| 2 + 5 | Sensitized, exposed to 105 μg or more OA/GP (n = 3) | 16.7 ± 7.6 |
| 3 | Non- sensitized, exposed to 105 μg OA/GP (n = 8) | 1.5 ± 1.3 |
| 4 | Sensitized, exposed to 70 μg OA/GP (n = 3) | 4.2 ± 1.6 |

Conclusions. Challenging GPs, previously sensitized with rabbit anti OA, with aerosolized OA for 1.5 minutes, induced within minutes following exposure a severe broncho-constriction, which led in the majority of GPs to death. Surviving GPs exhibited a large infiltration of eosinophils in the BAL.

Pretreatment of the GPs with aerosolized complement peptide C3a9 (app. 7 μg per GP) blocked the monitored respiratory distress, reduced the incidence of death and prevented almost completely the infiltration of eosinophils.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

REFERENCES

Barsumian et al, "IgE-induced histamine release from rat basophilic leukemia cell lines: isolation of releasing and non-releasing clones", *Eur J Immunol* 11(4):317–323 (1981)

Beaven et al, "Signal transduction by Fc receptors: the FcεRI case", *Immunol Today* 14(5):222–226 (1993)

Benhamou et al, "Protein-tyrosine phosphorylation: an essential component of FcεRI signaling", *Immunol Today* 13(6):195–197 (1992)

Bentley et al, "Immunohistology of the nasal mucosa in seasonal allergic rhinitis: increases in activated eosinophils and epithelial mast cells", *J Allergy Clin Immunol* 89(4):877–883 (1992)

Erdei et al, "Complement peptide C3a inhibits IgE-mediated triggering of rat mucosal mast cells", *Int Immunol* 7(9):1433–1439 (1995)

Gulbenkian et al, "Anaphylactic challenge causes eosinophil accumulation in bronchoalveolar lavage fluid of guinea pigs. Modulation by betamethasone, phenidone, indomethacin, WEB 2086, and a novel antiallergy agent, SCH 37224", *Am Rev Respir Dis* 142(3):680–685 (1990)

Holowka et al, "Recent evidence for common signaling mechanisms among immunoreceptors that recognize foreign antigens", *Cell Signal* 4(4):339–349 (1992)

Jouvin et al, "Differential control of the tyrosine kinases Lyn and Syk by the two signaling chains of the high affinity immunoglobulin E receptor", *J Biol Chem* 269(8):5918–5925 (1994)

Juliusson et al, "Proteinase content of mast cells of nasal mucosa; effects of natural allergen exposure and of local corticosteroid treatment", *Allergy* 50(1):15–22 (1995)

Kaiser, F. et al, "Color test for detection of free terminal amino groups in the solid-phase synthesis of peptides", *Anal. Biochem* 34(2):595–598 (1970)

Merrifield, R. B. *J Amer Chem Soc* 85:2149 (1963)

Mousli et al, "Peptidergic pathway in human skin and rat peritoneal mast cell activation", *Immunopharmacology* 27(1):1–11 (1994)

Ravetch et al, "Fc receptors", *Annu Rev Immunol* 9:457–492 (1991)

Rudolph et al, "Thirteen hybridomas secreting hapten-specific immunolobulin E from mice with $Ig^a$ or $Ig^b$ heavy chain haplotype", *Eur. J. Immunol* 11(6):527–529 (1981)

Schwartz, L. B., "Mast cells: function and contents", *Cur Opin Immunol* 6(1):91–97 (1994)

Turner, R. A., in *Screening Methods in Pharmacology* (1965)

Underwood et al, "SB 239063, a potent p38 MAP kinase inhibitor, reduces inflammatory cytokine production, airways eosinophil infiltration, and persistence", *J Pharmacol Exp Ther* 293(1):281–288 (2000)

What is claimed is:

1. A molecule consisting of:

(a) a peptide consisting of the sequence of amino acids 50–76 (residues 50–76 of SEQ ID NO:1) of the human complement C3a;

(b) a fragment of (a) having at least five amino acid residues in which one or more of the following deletions from (a) have been made: the residues at positions 50, 50–53, 50–54, 50–55, 50–56, 57–76, 61–76, 62–76, 63–76, 64–76, 65–76, 66–76, or 70–76, which fragment has the property of inhibiting the IgE-mediated triggering and/or the FcεRI-induced secretory response of mucosal mast cells;

(c) an analog of (a) or (b) in which one or more of the following additions and/or substitutions are made:

the Asp-Cys residues at 55–56 are substituted by Arg-Arg when at the N-terminus, the Cys residue at position 56 is substituted by Arg when at the N- or C-terminus, when a Cys residue at position 56 or 57 is at the N-terminus, it is acylated by a non-polar lower carboxylic acyl group, the Cys-Cys residues 56–57 are substituted by Ala-Ala or Ser-Ser, the Tyr residue at position 59 is substituted by another aromatic amino acid, the Ile residue at position 60 is substituted by Gly, the Thr residue at position 61 is substituted by Arg or, when at the C-terminus of the molecule, by Agm, the Glu residue at position 62 is substituted by Lys or Arg, the Leu residue at position 63 is substituted by Arg or, when at the C-terminus of the molecule, by Agm, the Arg residue at position 64 is substituted by any positively charged amino acid residue, the Arg residue at position 65 is substituted by Glu, the Ala residue at position 68 is substituted by Arg, the Arg residue at position 69 is substituted by Lys, the Ala residue at position 70 is substituted by Asp, the Ser residue at position 71 is substituted by His, the His residue at position 72 is substituted by Val, the Leu residue at position 73 is substituted by Ile, Ala or Gly, and an agmatine (Agm) residue is added at the C terminal side of the Ala at position 76, which analog has the property of inhibiting the IgE-mediated triggering and/or the FcεRI-induced secretory response of mucosal mast cells;

(d) a chemical derivative of (a), (b) or (c) formed by modification of a free carboxy, amino or hydroxy group of one or more amino acid residues so as to add one or more chemical moieties not normally a part of the peptide molecule, without changing one amino acid residue to a different amino acid residue, which derivative has the property of inhibiting the IgE-mediated triggering and/or the FcεRI-induced secretory response of mucosal mast cells; or (e) a salt of (a), (b), (c) or (d).

2. A molecule in accordance with claim 1 selected from the group of sequences consisting of:

(a) X1-Cys-Asn-R1-Ile-Thr-R2-Leu-R3-R4-Gln-His-R5-R6-R7-R8-R9-R10-Gly-Leu-Ala-R12 (SEQ ID NOs:28–30);

(b) X1-Cys-Asn-R1-X4 (SEQ ID NOs:5–13);

(c) X2-Lys-Val -Phe-Leu-Asp-X3 (SEQ ID NOs:14–17); and (d) X5-Asp-Ser-Ser-Asn-Tyr-Ile-R11 (SEQ ID NO:18) wherein X1 is H, lower alkanoyl, Cys, Asp-Cys or Arg-Arg-Cys;

X2 is H, lower alkanoyl or Lys;

X3 is (i) Arg, (ii) Ala-Ala-Asn-R1-Ile-Thr-R2-Leu-R3-R4 (residues 7–16 of SEQ ID NO:15), (iii) Cys-Cys-Asn-R1-Ile-Thr-2-Leu-R3 (residues 7–15 of SEQ ID NO:16), or (iv) Cys-Cys-Asn-R1-Ile-Thr-R2-Leu-R3-R4-Gln-His-R5-R6 (residues 7–20 of SEQ ID NO:17);

X4 is (i) Gly, (ii) Ile-Thr-R2-Leu-R3 (residues 5–9 of SEQ ID NO:6), or (iii) Ile-Thr-Arg-R11 (residues 5–8 of SEQ ID NO:7);

X5 is H, lower alkandyl or Leu;

R1 is an aromatic amino acid residue;

R2 is Glu or Lys;

R3 is a positively charged amino acid residue;

R4 is Arg or Glu;

R5 is Ala or Arg;

R6 is Arg or Lys;

R7 is Ala or Asp;

R8 is Ser or His;

R9 is His or Val;

R10 is Leu, Ile, Ala or Gly;

R11 is OH, Arg, Arg-$NH_2$, or Agm (agmatine); and

R12 is OH or Agm, or a chemical derivative or pharmaceutically acceptable salt thereof, wherein said chemical derivative is formed by modification of a free carboxy, amino or hydroxy group of one or more amino acid residues so as to add one or more chemical moieties not normally a part of the peptide molecule, without changing one amino acid residue to a different amino acid residue, which derivative has the property of inhibiting the IgE-mediated triggering and/or the FcεRI-induced secretory response of mucosal mast cells.

3. A molecule according to claim 2, wherein R1 is an aromatic amino acid residue selected from the group consisting of Phe, Tyr, His and Trp; and R3 is a positively charged amino acid residue selected from the group consisting of Arg, D-Arg, Har (homoarginine) and Lys.

4. The molecule according to claim 2 of the sequence: Cys-Asn-Tyr-Ile-Thr-Glu-Leu-Arg-Arg-Gln-His-Ala-Arg-Ala-Ser-His-Leu-Gly-Leu-Ala (residues 57–76 of SEQ ID NO:1).

5. The molecule according to claim 2 of the sequence: Cys-Asn-Tyr-Ile-Thr-Glu-Leu-Arg-Arg-Gln-His-Ala-Arg-Ala-Ser-His-Leu-Gly-Leu-Ala-$NH_2$ (residues 57–76 of SEQ ID NO:1).

6. The molecule according to claim 2 of the sequence: Asp-Cys-Cys-Asn-Tyr-Ile-Thr-Arg (SEQ ID NO:20).

7. The molecule according to claim 2 of the sequence:

Asp-Cys-Cys-Asn-Tyr-Ile-Thr-Arg-$NH_2$ (SEQ ID NO:20).

8. The molecule according to claim 2 of the sequence:

Asp-Ser-Ser-Asn-Tyr-Ile-Arg (SEQ ID NO:21).

9. The molecule according to claim 2 of the sequence:

Asp-Ser-Ser-Asn-Tyr-Ile-Arg-$NH_2$ (SEQ ID NO:21).

10. The molecule according to claim 2 of the sequence:

Cys-Cys-Asn-Tyr-Gly (SEQ ID NO:22).

11. The molecule according to claim 2 of the sequence:

Cys-Cys-Asn-Tyr-Gly-$NH_2$ (SEQ ID NO:22).

12. The molecule according to claim 1 of the sequence:

Asp-Ser-Ser-Asn-Tyr-Ile-Thr-Arg (SEQ ID NO:27).

13. A pharmaceutical composition comprising a molecule according to claim 1 and a pharmaceutically acceptable carrier.

14. A method for the treatment of allergic disorders caused by IgE mediated (Type I) hypersensitivity, where mucosal-type mast cells are involved, which method comprises administering to an individual in need thereof an effective amount of a molecule in accordance with claim 1.

15. A method in accordance with claim 14, wherein said molecule is selected from the group of sequences consisting of:

(a) X1-Cys-Asn-R1-Ile-Thr-R2-Leu-R3-R4-Gln-His-R5-R6-R7-R8-R9-R10-Gly-Leu-Ala-R12 (SEQ ID NOs:28–30);

(b) X1-Cys-Asn-R1-X4 (SEQ ID NOs:5–13);

(c) X2-Lys-Val-Phe-Leu-Asp-X3 (SEQ ID NOs:14–17); and (d) X5-Asp-Ser-Ser-Asn-Tyr-Ile-R11 (SEQ ID NO:18) wherein X1 is H, lower alkanoyl, Cys, Asp-Cys or Arg-Arg-Cys;

X2 is H, lower alkanoyl or Lys;

X3 is (i) Arg, (ii) Ala-Ala-Asn-R1-Ile-Thr-R2-Leu-R3-R4 (residues 7–16 of SEQ ID NO:15), (iii) Cys-Cys-Asn-R1-Ile-Thr-R2-Leu-R3 (residues 7–15 of SEQ ID NO:16), or (iv) Cys-Cys-Asn-R1-Ile-Thr-R2-Leu-R3-R4-Gln-His-R5-R6 (residues 7–20 of SEQ ID NO:17);

X4 is (i) Gly, (ii) Ile-Thr-R2-Leu-R3 (residues 5–9 of SEQ ID NO:6), or (iii) Ile-Thr-Arg-R11 (residues 5–8 of SEQ ID NO:7);

X5 is H, lower alkanoyl or Leu;

R1 is an aromatic amino acid residue;

R2 is Glu or Lys;

R3 is a positively charged amino acid residue;

R4 is Arg or Glu;

R5 is Ala or Arg;

R6 is Arg or Lys;

R7 is Ala or Asp;

R8 is Ser or His;

R9 is His or Val;

R10 is Leu, Ile, Ala or Gly;

R11 is OH, Arg, Arg-$NH_2$, or Agm (agmatine); and R12 is OH or Agm, or a chemical derivative or pharmaceutically acceptable salt thereof, wherein said chemical derivative is formed by modification of a free carboxy, amino or hydroxy group of one or more amino acid residues so as to add one or more chemical moieties not normally a part of the peptide molecule, without changing one amino acid residue to a different amino acid residue, which derivative has the property of inhibiting the IgE-mediated triggering and/or the FcεRI-induced secretory response of mucosal mast cells.

16. The method according to claim 15, wherein said molecule has the sequence:

Asp-Cys-Cys-Asn-Tyr-Ile-Thr-Arg (SEQ ID NO:20).

17. The method according to claim 14, wherein said molecule has the sequence:

Asp-Ser-Ser-Asn-Tyr-Ile-Thr-Arg (SEQ ID NO:27).

* * * * *

UNITED STATES PATENT AND TRADEMARK OFFICE

CERTIFICATE OF CORRECTION

PATENT NO. : 6,682,740 B1
DATED : January 27, 2004
INVENTOR(S) : Erdei et al.

It is certified that error appears in the above-identified patent and that said Letters Patent is hereby corrected as shown below:

Title page,
Item [54], Title, delete "FRAM" and insert therefor -- FROM --

Signed and Sealed this

Fifteenth Day of June, 2004

JON W. DUDAS
*Acting Director of the United States Patent and Trademark Office*

SEQUENCE LISTING

```
<160> NUMBER OF SEQ ID NOS:  30

<210> SEQ ID NO 1
<211> LENGTH: 77
<212> TYPE: PRT
<213> ORGANISM: Homo sapiens

<400> SEQUENCE: 1

Ser Val Gln Leu Thr Glu Lys Arg Met Asp Lys Val Gly Lys Tyr Pro
  1               5                  10                  15

Lys Glu Leu Arg Lys Cys Cys Glu Asp Gly Met Arg Glu Asn Pro Met
             20                  25                  30

Arg Phe Ser Cys Gln Arg Arg Thr Arg Phe Ile Ser Leu Gly Glu Ala
         35                  40                  45

Cys Lys Lys Val Phe Leu Asp Cys Cys Asn Tyr Ile Thr Glu Leu Arg
     50                  55                  60

Arg Gln His Ala Arg Ala Ser His Leu Gly Leu Ala Arg
 65                  70                  75


<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 1 is either present or absent.
      When Xaa at pos. 1 is present it is Cys; when Xaa at
      pos. 1 is absent, the Cys at pos. 2 may be modified
      with a lower alkanoyl group.
<223> OTHER INFORMATION: Xaa at pos. 4 is an aromatic amino acid
      residue; Xaa at pos. 7 is Glu or Lys; Xaa at pos. 9 is a
      positively charged amino acid residue; Xaa at pos.
      10 is Arg or Glu; Xaa at pos. 13 is Ala or Arg;
<223> OTHER INFORMATION: Xaa at pos. 14 is Arg or Lys; Xaa at pos. 15 is
      Ala or Asp; Xaa at pos. 16 is Ser or His; Xaa at
      pos. 17 is His or Val; Xaa at pos. 18 is Leu, Ile,
      Ala or Gly; Xaa at pos. 22 is either present or

<400> SEQUENCE: 2

Xaa Cys Asn Xaa Ile Thr Xaa Leu Xaa Xaa Gln His Xaa Xaa Xaa Xaa
  1               5                  10                  15

Xaa Xaa Gly Leu Ala Xaa
             20


<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 5 is an aromatic amino acid
      residue; Xaa at pos. 8 is Glu or Lys;  Xaa at pos. 10 is a
      positively charged amino acid residue; Xaa at pos.
      11 is Arg or Glu; Xaa at pos. 14 is Ala or Arg;
<223> OTHER INFORMATION: Xaa at pos. 15 is Arg or Lys; Xaa at pos. 16 is
      Ala or Asp; Xaa at pos. 17 is Ser or His; Xaa at
      pos. 18 is His or Val; Xaa at pos. 19 is Leu, Ile,
      Ala or Gly; Xaa at pos. 23 is either absent or

<400> SEQUENCE: 3

Asp Cys Cys Asn Xaa Ile Thr Xaa Leu Xaa Xaa Gln His Xaa Xaa Xaa
  1               5                  10                  15

Xaa Xaa Xaa Gly Leu Ala Xaa
             20
```

-continued

```
<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 6 is an aromatic amino acid
      residue; Xaa at pos. 9 is Glu or Lys; Xaa at pos. 11 is a
      positively charged amino acid residue; Xaa at pos.
      12 is Arg or Glu; Xaa at pos. 15 is Ala or Arg;
<223> OTHER INFORMATION: Xaa at pos. 16 is Arg or Lys; Xaa at pos. 17 is
      Ala or Asp; Xaa at pos. 18 is Ser or His; Xaa at
      pos. 19 is His or Val; Xaa at pos. 20 is Leu, Ile,
      Ala or Gly; Xaa at pos. 24 is either absent or

<400> SEQUENCE: 4

Arg Arg Cys Cys Asn Xaa Ile Thr Xaa Leu Xaa Xaa Gln His Xaa Xaa
  1               5                  10                  15

Xaa Xaa Xaa Xaa Gly Leu Ala Xaa
             20


<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 1 is either present or absent.
      When Xaa at pos. 1 is present it is Cys; when Xaa at
      pos. 1 is absent, the Cys at pos. 2 may be modified
      with a lower alkanoyl group.
<223> OTHER INFORMATION: Xaa at pos. 4 is an aromatic amino acid residue

<400> SEQUENCE: 5

Xaa Cys Asn Xaa Gly
  1               5


<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 1 is either present or absent.
      When Xaa at pos. 1 is present it is Cys; when Xaa at
      pos. 1 is absent, the Cys at pos. 2 may be modified
      with a lower alkanoyl group.
<223> OTHER INFORMATION: Xaa at pos. 4 is an aromatic amino acid
      residue; Xaa at pos. 7 is Glu or Lys; Xaa at pos. 9 is a
      positively charged amino acid residue

<400> SEQUENCE: 6

Xaa Cys Asn Xaa Ile Thr Xaa Leu Xaa
  1               5


<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 1 is either present or absent.
      When Xaa at pos. 1 is present it is Cys; when Xaa at
      pos. 1 is absent, the Cys at pos. 2 may be modified
      with a lower alkanoyl group.
<223> OTHER INFORMATION: Xaa at pos. 4 is an aromatic amino acid
      residue; Xaa at pos. 8 is either present or absent.  When
      Xaa at pos. 8 is present it is Arg, Arg-NH2,
      or Agm (agmatine).

<400> SEQUENCE: 7
```

-continued

```
Xaa Cys Asn Xaa Ile Thr Arg Xaa
  1               5


<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 5 is an aromatic amino acid residue

<400> SEQUENCE: 8

Asp Cys Cys Asn Xaa Gly
  1               5


<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 5 is an aromatic amino acid
      residue; Xaa at pos. 8 is Glu or Lys; Xaa at pos. 10 is a
      positively charged amino acid residue

<400> SEQUENCE: 9

Asp Cys Cys Asn Xaa Ile Thr Xaa Leu Xaa
  1               5                   10


<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 5 is an aromatic amino acid
      residue; Xaa at pos. 9 is either present or absent.  When
      Xaa at pos. 9 is present it is Arg, Arg-NH2,
      or Agm (agmatine).

<400> SEQUENCE: 10

Asp Cys Cys Asn Xaa Ile Thr Arg Xaa
  1               5


<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 6 is an aromatic amino acid
      residue

<400> SEQUENCE: 11

Arg Arg Cys Cys Asn Xaa Gly
  1               5


<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 6 is an aromatic amino acid
      residue; Xaa at pos. 9 is Glu or Lys; Xaa at pos. 11 is a
      positively charged amino acid residue

<400> SEQUENCE: 12
```

-continued

```
Arg Arg Cys Cys Asn Xaa Ile Thr Xaa Leu Xaa
  1               5                  10


<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 6 is an aromatic amino acid
      residue; Xaa at pos. 10 is either present or absent.  When
      Xaa at pos. 10 is present it is Arg, Arg-NH2,
      or Agm (agmatine).

<400> SEQUENCE: 13

Arg Arg Cys Cys Asn Xaa Ile Thr Arg Xaa
  1               5                  10


<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 1 is either present or absent.
      When Xaa at pos. 1 is present it is Lys; when Xaa at
      pos. 1 is absent, the Lys at pos. 2 may be modified
      with a lower alkanoyl group.

<400> SEQUENCE: 14

Xaa Lys Val Phe Leu Asp Arg
  1               5


<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 1 is either present or absent.
      When Xaa at pos. 1 is present it is Lys; when Xaa at
      pos. 1 is absent, the Lys at pos. 2 may be modified
      with a lower alkanoyl group.
<223> OTHER INFORMATION: Xaa at pos. 10 is an aromatic amino acid
      residue; Xaa at pos. 13 is Glu or Lys; Xaa at pos. 15 is a
      positively charged amino acid residue; Xaa at pos.
      16 is Arg or Glu

<400> SEQUENCE: 15

Xaa Lys Val Phe Leu Asp Ala Ala Asn Xaa Ile Thr Xaa Leu Xaa Xaa
  1               5                  10                  15


<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 1 is either present or absent. When
      Xaa at pos. 1 is present it is Lys; when Xaa at
      pos. 1 is absent, the Lys at pos. 2 may be modified
      with a lower alkanoyl group.
<223> OTHER INFORMATION: Xaa at pos. 10 is an aromatic amino acid
      residue; Xaa at pos. 13 is Glu or Lys; Xaa at pos. 15 is a
      positively charged amino acid residue

<400> SEQUENCE: 16

Xaa Lys Val Phe Leu Asp Cys Cys Asn Xaa Ile Thr Xaa Leu Xaa
  1               5                  10                  15
```

-continued

```
<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 1 is either present or absent.
      When Xaa at pos. 1 is present it is Lys; when Xaa at
      pos. 1 is absent, the Lys at pos. 2 may be modified
      with a lower alkanoyl group.
<223> OTHER INFORMATION: Xaa at pos. 10 is an aromatic amino acid
      residue; Xaa at pos. 13 is Glu or Lys; Xaa at pos. 15 is a
      positively charged amino acid residue; Xaa at pos.
      16 is Arg or Glu; Xaa at pos. 19 is Ala or Arg;
<223> OTHER INFORMATION: Xaa at pos. 20 is Arg or Lys

<400> SEQUENCE: 17

Xaa Lys Val Phe Leu Asp Cys Cys Asn Xaa Ile Thr Xaa Leu Xaa Xaa
  1               5                  10                  15

Gln His Xaa Xaa
             20


<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 1 is either present or absent.
      When Xaa at pos. 1 is present it is Leu; when Xaa at
      pos. 1 is absent, the Asp at pos. 2 may be modified
      with a lower alkanoyl group.
<223> OTHER INFORMATION: Xaa at pos. 8 is either present or absent.
      When Xaa at pos. 8 is present it is Arg, Arg-NH2,
      or Agm (agmatine).

<400> SEQUENCE: 18

Xaa Asp Ser Ser Asn Tyr Ile Xaa
  1               5


<210> SEQ ID NO 19
<211> LENGTH: 21
<212> TYPE: PRT
<213> ORGANISM: Homo sapiens
<220> FEATURE:
<223> OTHER INFORMATION: Residue 21 may be amidated

<400> SEQUENCE: 19

Cys Asn Tyr Ile Thr Lys Leu Arg Glu Gln His Arg Arg Asp His Val
  1               5                  10                  15

Leu Gly Leu Ala Arg
             20


<210> SEQ ID NO 20
<211> LENGTH: 8
<212> TYPE: PRT
<213> ORGANISM: Homo sapiens
<220> FEATURE:
<223> OTHER INFORMATION: Residue 8 may be amidated

<400> SEQUENCE: 20

Asp Cys Cys Asn Tyr Ile Thr Arg
  1               5


<210> SEQ ID NO 21
<211> LENGTH: 7
<212> TYPE: PRT
<213> ORGANISM: Homo sapiens
<220> FEATURE:
```

-continued

<223> OTHER INFORMATION: Residue 7 may be amidated

<400> SEQUENCE: 21

Asp Ser Ser Asn Tyr Ile Arg
1 5

<210> SEQ ID NO 22
<211> LENGTH: 5
<212> TYPE: PRT
<213> ORGANISM: Homo sapiens
<220> FEATURE:
<223> OTHER INFORMATION: Residue 5 may be amidated

<400> SEQUENCE: 22

Cys Cys Asn Tyr Gly
1 5

<210> SEQ ID NO 23
<211> LENGTH: 15
<212> TYPE: PRT
<213> ORGANISM: Homo sapiens
<220> FEATURE:
<223> OTHER INFORMATION: Residue 15 may be amidated

<400> SEQUENCE: 23

Lys Val Phe Leu Asp Ala Ala Asn Tyr Ile Thr Glu Leu Arg Arg
1 5 10 15

<210> SEQ ID NO 24
<211> LENGTH: 7
<212> TYPE: PRT
<213> ORGANISM: Homo sapiens
<220> FEATURE:
<223> OTHER INFORMATION: Residue 7 may be amidated

<400> SEQUENCE: 24

Lys Lys Val Phe Leu Asp Arg
1 5

<210> SEQ ID NO 25
<211> LENGTH: 10
<212> TYPE: PRT
<213> ORGANISM: Homo sapiens
<220> FEATURE:
<223> OTHER INFORMATION: Residue 10 may be amidated

<400> SEQUENCE: 25

Arg Arg Cys Cys Asn Tyr Ile Thr Arg Arg
1 5 10

<210> SEQ ID NO 26
<211> LENGTH: 6
<212> TYPE: PRT
<213> ORGANISM: Homo sapiens
<220> FEATURE:
<223> OTHER INFORMATION: Residue 6 may be amidated

<400> SEQUENCE: 26

Asp Cys Cys Asn Tyr Gly
1 5

<210> SEQ ID NO 27
<211> LENGTH: 8
<212> TYPE: PRT
<213> ORGANISM: Homo sapiens
<220> FEATURE:
<223> OTHER INFORMATION: Residue 6 may be amidated -continued

<400> SEQUENCE: 27

Asp Ser Ser Asn Tyr Ile Thr Arg
1 5

<210> SEQ ID NO 28
<211> LENGTH: 22
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 1 is either present or absent. When Xaa at pos. 1 is present it is Cys; when Xaa at pos. 1 is absent, the Cys at pos. 2 may be modified with a lower alkanoyl group.
<223> OTHER INFORMATION: Xaa at pos. 4 is an aromatic amino acid residue; Xaa at pos. 7 is Glu or Lys; Xaa at pos. 9 is a positively charged amino acid residue; Xaa at pos. 10 is Arg or Glu; Xaa at pos. 13 is Ala or Arg;
<223> OTHER INFORMATION: Xaa at pos. 14 is Arg or Lys; Xaa at pos. 15 is Ala or Asp; Xaa at pos. 16 is Ser or His; Xaa at pos. 17 is His or Val; Xaa at pos. 18 is Leu, Ile, Ala or Gly; Xaa at pos. 22 is either present or

<400> SEQUENCE: 28

Xaa Cys Asn Xaa Ile Thr Xaa Leu Xaa Xaa Gln His Xaa Xaa Xaa Xaa
1 5 10 15

Xaa Xaa Gly Leu Ala Xaa
20

<210> SEQ ID NO 29
<211> LENGTH: 23
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 5 is an aromatic amino acid residue; Xaa at pos. 8 is Glu or Lys; Xaa at pos. 10 is a positively charged amino acid residue; Xaa at pos. 11 is Arg or Glu; Xaa at pos. 14 is Ala or Arg;
<223> OTHER INFORMATION: Xaa at pos. 15 is Arg or Lys; Xaa at pos. 16 is Ala or Asp; Xaa at pos. 17 is Ser or His; Xaa at pos. 18 is His or Val; Xaa at pos. 19 is Leu, Ile, Ala or Gly; Xaa at pos. 23 is either absent or

<400> SEQUENCE: 29

Asp Cys Cys Asn Xaa Ile Thr Xaa Leu Xaa Xaa Gln His Xaa Xaa Xaa
1 5 10 15

Xaa Xaa Xaa Gly Leu Ala Xaa
20

<210> SEQ ID NO 30
<211> LENGTH: 24
<212> TYPE: PRT
<213> ORGANISM: Artificial Sequence
<220> FEATURE:
<223> OTHER INFORMATION: Description of Artificial Sequence: synthetic
<223> OTHER INFORMATION: Xaa at pos. 6 is an aromatic amino acid residue; Xaa at pos. 9 is Glu or Lys; Xaa at pos. 11 is a positively charged amino acid residue; Xaa at pos. 12 is Arg or Glu; Xaa at pos. 15 is Ala or Arg;
<223> OTHER INFORMATION: Xaa at pos. 16 is Arg or Lys; Xaa at pos. 17 is Ala or Asp; Xaa at pos. 18 is Ser or His; Xaa at pos. 19 is His or Val; Xaa at pos. 20 is Leu, Ile, Ala or Gly; Xaa at pos. 24 is either absent or

<400> SEQUENCE: 30

Arg Arg Cys Cys Asn Xaa Ile Thr Xaa Leu Xaa Xaa Gln His Xaa Xaa
1 5 10 15

-continued

```
Xaa Xaa Xaa Xaa Gly Leu Ala Xaa
            20
```